US010294472B2

(12) United States Patent
Ichiki et al.

(10) Patent No.: US 10,294,472 B2
(45) Date of Patent: May 21, 2019

(54) NUCLEIC ACID LINKER

(71) Applicants: The University of Tokyo, Bunkyo-ku, Tokyo (JP); Nikon Corporation, Chiyoda-ku, Tokyo (JP)

(72) Inventors: Takanori Ichiki, Tokyo (JP); Shingo Ueno, Tokyo (JP); Manish Biyani, Tokyo (JP); Ryo Kobayashi, Tokyo (JP); Hirofumi Shiono, Tokyo (JP)

(73) Assignees: THE UNIVERSITY OF TOKYO, Tokyo (JP); NIKON CORPORATION, Tokyo (JP)

( * ) Notice: Subject to any disclaimer, the term of this patent is extended or adjusted under 35 U.S.C. 154(b) by 657 days.

(21) Appl. No.: 14/849,992

(22) Filed: Sep. 10, 2015

(65) Prior Publication Data

US 2016/0076022 A1 Mar. 17, 2016

Related U.S. Application Data

(63) Continuation of application No. PCT/JP2014/055943, filed on Mar. 7, 2014.

(30) Foreign Application Priority Data

Mar. 13, 2013 (JP) .................. 2013-050936

(51) Int. Cl.
*C12N 15/10* (2006.01)
*C12Q 1/6853* (2018.01)

(52) U.S. Cl.
CPC ..... *C12N 15/1062* (2013.01); *C12N 15/1093* (2013.01); *C12Q 1/6853* (2013.01)

(58) Field of Classification Search
CPC .................................................. C12N 15/062

USPC ........................................................ 536/23.1
See application file for complete search history.

(56) References Cited

U.S. PATENT DOCUMENTS

| 6,416,950 B1 | 7/2002 | Lohse et al. |
| 2002/0182687 A1 | 12/2002 | Kurz et al. |
| 2008/0312103 A1 | 12/2008 | Nemoto et al. |
| 2010/0105569 A1 | 4/2010 | Hsieh et al. |
| 2011/0183863 A1 | 7/2011 | Wagner et al. |

(Continued)

FOREIGN PATENT DOCUMENTS

| JP | 2003-505094 A | 2/2003 |
| JP | 4318721 B2 | 6/2009 |
| JP | 4808315 B2 | 8/2011 |

(Continued)

OTHER PUBLICATIONS

Office Action dated May 31, 2016, in JP 2015-505439, with English translation.

(Continued)

*Primary Examiner* — Jezia Riley
(74) *Attorney, Agent, or Firm* — Foley & Lardner LLP

(57) ABSTRACT

The present invention relates to a nucleic acid linker for producing a complex of mRNA, and a protein or a peptide which is encoded by the mRNA, the linker comprising: a spacer portion at the 5'-terminal; a polynucleotide portion hybridizable with at least a part of a sequence of the mRNA; and an arm portion which has a connection portion for the protein or the peptide at the 3'-terminal, in which the spacer portion, the polynucleotide portion, and the arm portion form a single strand, and in which the polynucleotide portion contains a photoreactive base derivative.

7 Claims, 19 Drawing Sheets

Specification includes a Sequence Listing.

(56) References Cited

U.S. PATENT DOCUMENTS

2014/0235508 A1 8/2014 Nemoto et al.
2014/0296111 A1 10/2014 Ueno et al.

FOREIGN PATENT DOCUMENTS

| JP | 2011-217708 A | 11/2011 |
|----|---------------|---------|
| JP | 2011-528912 A | 12/2011 |
| JP | 2012-504415 A | 2/2012 |
| WO | WO 00/32823 A1 | 6/2000 |
| WO | WO 2010/011944 A2 | 1/2010 |
| WO | WO 2013/065827 A1 | 5/2013 |

OTHER PUBLICATIONS

Supplementary European Search Report dated Jun. 20, 2016, in EP 14762773.1.
International Search Report dated Jun. 10, 2014 in PCT/JP2014/055943.
Written Opinion dated Jun. 10, 2014 in PCT/JP2014/055943.
Kore et al., "Efficient synthesis of 3-cyanovinylcarbazole-1'-β-deoxyriboside-5'-triphosphate: a reversible photo-cross-linking probe," Tetrahedron Letters, 2012, 53:4012-4014.
Nemoto et al., "In vitro virus: Bonding of mRNA bearing puromycin at the 3'-terminal end to the C-terminal end of its encoded protein on the ribosome in vitro," FEBS Letters, 1997, 414:405-408.
Yamaguchi et al., "cDNA display: a novel screening method for functional disulfide-rich peptides by solid-phase synthesis and stabilization of mRNA-protein fusions," Nucleic Acids Research, Jun. 15, 2009, 37(16):e108, 13 pages.

NUCLEIC ACID LINKER

CROSS-REFERENCE TO RELATED APPLICATION

This is a Continuation application of International Patent Application No. PCT/JP2014/055943 filed on Mar. 7, 2014, which claims priority on Japanese Patent Application No. 2013-050936 filed on Mar. 13, 2013. The contents of the aforementioned applications are incorporated herein by reference.

SEQUENCE LISTING

The instant application contains a Sequence Listing which has been submitted electronically in ASCII format and is hereby incorporated by reference in its entirety. Said ASCII copy, created on Nov. 11, 2015, is named 107929-0116_SL.txt and is 5,663 bytes in size.

BACKGROUND OF THE INVENTION

Field of the Invention

The present invention relates to a nucleic acid linker, a nucleic acid linker-reverse transcription primer complex, an mRNA-nucleic acid linker-reverse transcription primer complex, a nucleic acid linker-immobilized solid phase, a nucleic acid linker-reverse transcription primer complex-immobilized solid phase, a protein- or peptide-immobilized solid phase, a microarray, a nucleic acid recovery method, and a method of identifying a functional protein or a functional peptide.

Description of the Related Art

A new functional protein is expected to contribute to pharmaceutical products, detergents, food processing, reagents for research and development, clinical analysis, and various biological application fields such as bioenergy and biosensors.

When obtaining a new functional protein, a protein engineering technique for designing a protein using human knowledge from structural information of a protein has been mainly used. However, it is necessary to more efficiently screen a protein than in the technique in the related art in order to obtain a more useful protein, and a molecular evolution engineering technique which repeats modification and selection of a random molecular structure of a protein is expected.

A cDNA display method which is one of molecular evolution engineering techniques is a method of homologizing a genotype and a phenotype, in which a nucleic acid linker bonds a protein (phenotype), mRNA which encodes the protein, and cDNA (genotype) which is reverse-transcribed, together. The structure of an mRNA/cDNA-protein conjugant is extremely stable. Therefore, it is possible to carry out screening under various environments using the nucleic acid linker.

The cDNA display method has a characteristic in puromycin included in a nucleic acid linker which connects a protein with polynucleotide which encodes the protein (refer to PATENT LITERATURE 1).

Puromycin is a protein synthesis inhibitor having a structure similar to the 3'-terminal of aminoacyl-tRNA and is covalently bound specifically to the C-terminal of a protein under elongation on a ribosome under predetermined conditions.

The method of screening a useful protein using the cDNA display method has a series of the following processes.

First, a complex (mRNA-nucleic acid linker-protein complex) is generated in which a nucleic acid linker having puromycin is connected to mRNA; a protein is synthesized from the mRNA using a cell-free translation system; and the synthesized protein and the mRNA which encodes the synthesized protein are bound together through puromycin (refer to NON-PATENT LITERATURE 1).

Next, a library of the mRNA-nucleic acid linker-protein complex is produced, and then, the produced mRNA-nucleic acid linker-protein complex is reverse-transcribed by reverse transcriptase, and cDNA is synthesized to produce a library of mRNA/cDNA-nucleic acid linker-protein complex.

Next, a protein which has a desired function is selected using the library of the mRNA/cDNA-nucleic acid linker-protein complex and is identified by analyzing the base sequence of cDNA in the selected mRNA/cDNA-nucleic acid linker-protein complex. The timing for reverse transcription may be after the protein is selected (refer to NON-PATENT LITERATURE 2).

A protein array in which the above-described library of the mRNA/cDNA-nucleic acid linker-protein complex is immobilized on a substrate is important as a tool for obtaining a functional protein or a functional peptide in a short period of time through comprehensive analysis.

As a method for producing the protein array, a method has been proposed which uses a nucleic acid linker/reverse transcriptase primer structure having psoralen, which is a photoreactive base derivative, at the 5'-terminal (refer to PATENT LITERATURE 2). This method is excellent in that it is possible to improve synthetic efficiency of an mRNA-nucleic acid linker-protein or peptide complex by crosslinking a nucleic acid linker and mRNA and strengthening the bonding between the nucleic acid linker and the mRNA.

Patent Literature

[PATENT LITERATURE 1] Japanese Patent No. 4318721
[PATENT LITERATURE 2] Japanese Patent No. 4808315

Non-Patent Literature

[NON-PATENT LITERATURE 1] Nemoto, et. al., FEBS Lett, Vol. 414, pp. 405 to 408, 1997
[NON-PATENT LITERATURE 2] Yamaguchi, et. al., Nucleic Acids Res., Vol. 37, e. 108, 2009

SUMMARY OF THE INVENTION

However, in PATENT LITERATURE 2, there is no examination of efficiently producing an mRNA-nucleic acid linker-protein complex on a solid phase. Therefore, there is still room for improving a nucleic acid linker which efficiently synthesizes the mRNA-nucleic acid linker-protein or peptide complex on a solid phase.

The present invention provide a nucleic acid linker which efficiently synthesizes an mRNA-nucleic acid linker-protein or peptide complex on a solid phase, a nucleic acid linker-reverse transcription primer complex using the nucleic acid linker, an mRNA-nucleic acid linker-reverse transcription primer complex, a nucleic acid linker-immobilized solid phase, a nucleic acid linker-reverse transcription primer complex-immobilized solid phase, a protein- or peptide-immobilized solid phase, a microarray, a nucleic acid recovery method, and a method of identifying a functional protein or a functional peptide.

An embodiment of the present invention provides the following (1) to (15).

(1) A nucleic acid linker an embodiment of the present invention is a nucleic acid linker for producing a complex of mRNA, and a protein or a peptide which is encoded by the mRNA, characterized in that it comprises a spacer portion at the 5'-terminal; a polynucleotide portion hybridizable with at least a part of a sequence of the mRNA; and an arm portion which has a connection portion for the protein or the peptide at the 3'-terminal, wherein the spacer portion, the polynucleotide portion, and the arm portion form a single strand, and the polynucleotide portion contains a photoreactive base derivative.

(2) A nucleic acid linker of an embodiment of the present invention is a nucleic acid linker for producing a complex of mRNA, and a protein or a peptide which is encoded by the mRNA, characterized in that a polynucleotide portion hybridizable with at least a part of a sequence of the mRNA, and an arm portion having a connection portion for the protein or the peptide form a single strand, the polynucleotide portion contains a photoreactive base derivative, and the photoreactive base derivative is a 3-cyanovinylcarbazole nucleoside.

(3) A nucleic acid linker-reverse transcription primer complex of an embodiment of the present invention is characterized in that it is formed of the nucleic acid linker and a reverse transcription primer of the mRNA, and the reverse transcription primer includes a 5'-terminal region portion having a sequence hybridizable with at least a part of a sequence of the arm portion of the nucleic acid linker.

(4) An mRNA-nucleic acid linker-reverse transcription primer complex of an embodiment of the present invention is formed of the nucleic acid linker, the mRNA, and a reverse transcription primer of the mRNA, characterized in that the reverse transcription primer comprises a 5'-terminal region portion having a sequence hybridizable with at least a part of a sequence of an arm portion of the nucleic acid linker, and a 3'-terminal region portion having a sequence hybridizable with at least a part of a sequence of the mRNA.

(5) A nucleic acid linker-immobilized solid phase of an embodiment of the present invention is characterized in that the nucleic acid linker is immobilized on a solid phase.

(6) A nucleic acid linker-reverse transcription primer complex-immobilized solid phase of an embodiment of the present invention is characterized in that the nucleic acid linker-reverse transcription primer complex is immobilized on a solid phase.

(7) A protein- or peptide-immobilized solid phase of an embodiment of the present invention is characterized in that a complex of mRNA, the nucleic acid linker, and a protein or a peptide which is encoded by the mRNA is immobilized on a solid phase.

(8) A protein- or peptide-immobilized solid phase of an embodiment of the present invention is characterized in that a mRNA-nucleic acid linker-protein- or peptide-reverse transcription primer complex, which is a complex of the above-described mRNA-nucleic acid linker-reverse transcription primer complex and a protein or a peptide which is encoded by the mRNA, is immobilized on a solid phase.

(9) A microarray of an embodiment of the present invention is a microarray in which a plurality of nucleic acid linkers are immobilized, characterized in that the nucleic acid linkers are the above-described nucleic acid linkers.

(10) A microarray of an embodiment of the present invention is a microarray in which a plurality of nucleic acid linker-reverse transcription primer complexes are immobilized, characterized in that the nucleic acid linker-reverse transcription primer complexes are the above-described nucleic acid linker-reverse transcription primer complexes.

(11) A microarray of an embodiment of the present invention is a microarray in which a plurality of mRNA-nucleic acid linker-protein complexes are immobilized, is characterized in that the mRNA-nucleic acid linker-protein complexes are the complexes of the above-described nucleic acid linkers and proteins or peptides which are encoded by the mRNA.

(12) A method of recovering a nucleic acid of an embodiment of the present invention is a method of recovering a nucleic acid, comprising: providing a mRNA, and a solid phase on which the above-described nucleic acid linker is immobilized; (A1) photocrosslinking the mRNA and the nucleic acid linker using a photoreactive base derivative; and (B1) dissociating the photocrosslinking of the mRNA and the nucleic acid linker through light irradiation.

(13) A method of recovering a nucleic acid of an embodiment of the present invention is a method of recovering a nucleic acid, comprising: providing a solid phase on which the mRNA-nucleic acid linker-reverse transcription primer complex; (A2) photocrosslinking the reverse transcription primer of the mRNA and the nucleic acid linker using a photoreactive base derivative; and (B2) dissociating the photocrosslinking of the reverse transcription primer and the nucleic acid linker through light irradiation.

(14) A method of identifying a functional protein or a functional peptide of an embodiment of the present invention is characterized in that it comprises (A6) bringing mRNA into contact with the above-described nucleic acid linker-immobilized solid phase and hybridizing the mRNA with the nucleic acid linker to form an mRNA-nucleic acid linker complex on the solid phase; (B6) synthesizing a protein or a peptide from the mRNA using a cell-free protein translation system and bonding the C-terminal of the protein or the peptide to a connection portion for the protein or the peptide to form an mRNA-nucleic acid linker-protein or peptide complex; (C6) bringing a reverse transcription primer, which is formed of a 5'-terminal region portion having a sequence hybridizable with at least a part of a sequence of an arm portion of the nucleic acid linker, and contains 3-cyanovinylcarbazole nucleoside, and a 3'-terminal region portion having a sequence hybridizable with at least a part of a sequence of the mRNA, into contact with the solid phase to form an mRNA-nucleic acid linker-protein- or peptide-reverse transcription primer complex; (D6) irradiating all spots on the solid phase with light in a first wavelength band to crosslink the nucleic acid linker and the mRNA and crosslink the nucleic acid linker and the reverse transcription primer; (E6) synthesizing cDNA which is obtained such that a complementary strand is elongated from the 3'-terminal of the reverse transcription primer by subjecting the mRNA-nucleic acid linker-protein- or peptide-reverse transcription primer complex to a reverse transcription reaction to produce an mRNA/cDNA-nucleic acid linker-protein or peptide complex; (F6) of subjecting the solid phase, on which the mRNA/cDNA-nucleic acid linker-protein or peptide complex is immobilized, to functional screening to specify a spot on the solid phase; (G6) irradiating the spot, which is specified through the functional screening, with light in a second wavelength band to dissociate the cDNA from the cDNA-nucleic acid linker-protein or peptide complex in the specified spot; and (H6) recovering the dissociated cDNA to analyze a base sequence thereof.

(15) A method of identifying a functional protein or a functional peptide of an embodiment of the present invention is characterized in that it comprises (A7) bringing mRNA into contact with the above-described nucleic acid linker-immobilized solid phase and hybridizing the mRNA with the nucleic acid linker to form an mRNA-nucleic acid linker complex on the solid phase; (B7) synthesizing a protein or a peptide from the mRNA using a cell-free protein translation system and bonding the C-terminal of the protein or the peptide to a connection portion for the protein or the peptide to form an mRNA-nucleic acid linker-protein or peptide complex; (C7) bringing a reverse transcription primer, which is formed of a 5"-terminal region portion having a sequence hybridizable with at least a part of a sequence of an arm portion of the nucleic acid linker, and contains 3-cyanovinylcarbazole nucleoside, and a 3'-terminal region portion having a sequence hybridizable with at least a part of a sequence of the mRNA, into contact with the solid phase to form an mRNA-nucleic acid linker-protein- or peptide-reverse transcription primer complex; (D7) synthesizing cDNA which is obtained such that a complementary strand is elongated from the 3'-terminal of the reverse transcription primer by subjecting the mRNA-nucleic acid linker-protein- or peptide-reverse transcription primer complex to a reverse transcription reaction to produce an mRNA/cDNA-nucleic acid linker-protein or peptide complex; (E7) subjecting the solid phase, on which the mRNA/cDNA-nucleic acid linker-protein or peptide complex is immobilized, to functional screening to specify a spot on the solid phase; (F7) irradiating a spot other than the spot, which is specified through the functional screening, with light in a first wavelength band to crosslink the nucleic acid linker and the cDNA; (G7) dissociating the cDNA from the cDNA-nucleic acid linker-protein or peptide complex in the specific spot; and (H7) recovering the dissociated cDNA to analyze a base sequence thereof.

DESCRIPTION OF THE EMBODIMENTS

Nucleic Acid Linker

First Embodiment

A nucleic acid linker of the present embodiment is a nucleic acid linker for producing a complex of mRNA, and a protein or a peptide which is encoded by the mRNA. The structure of the nucleic acid linker of the present embodiment will be described using FIG. 1.

Figure 1:
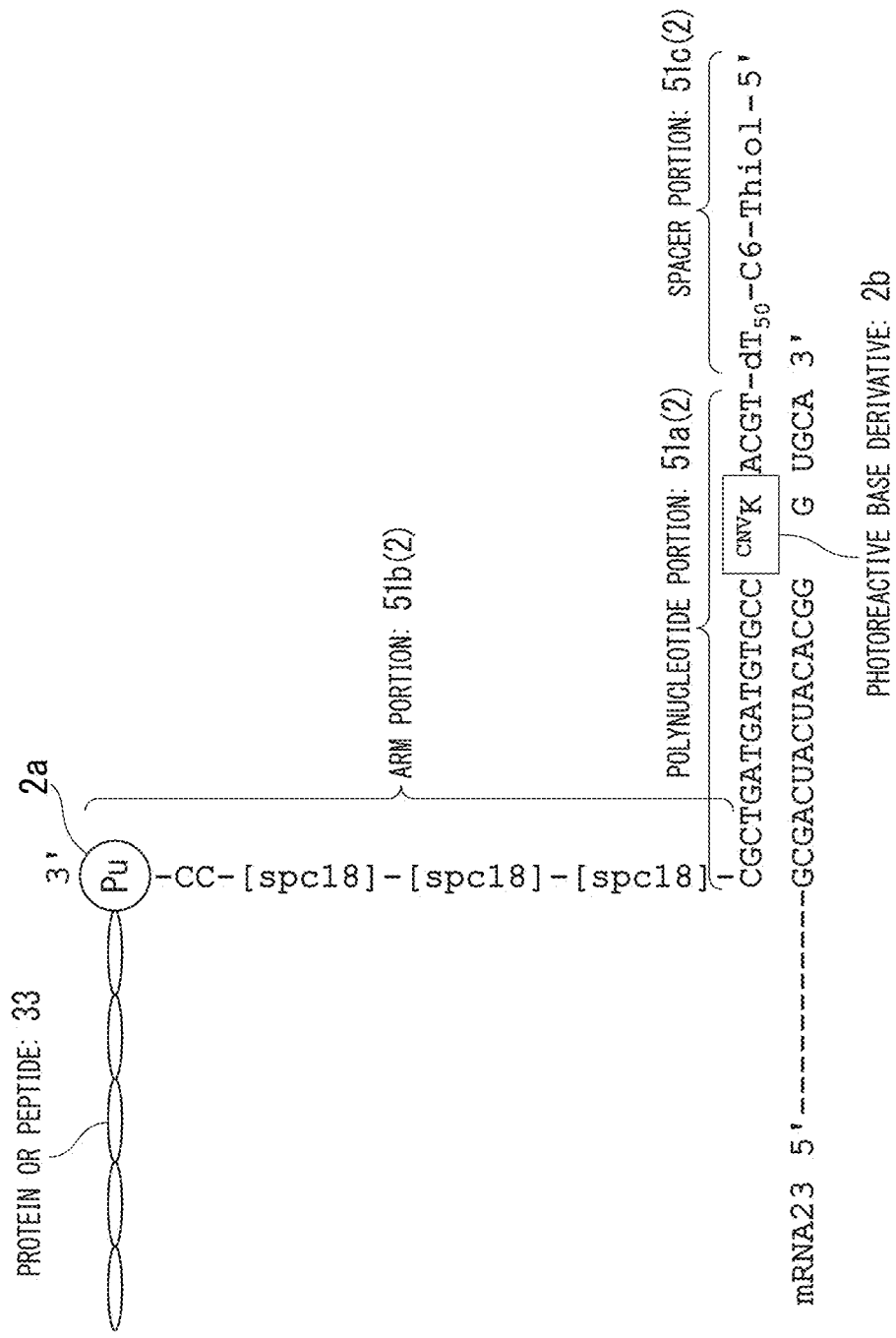
FIG. 1 is a view showing a mode of a nucleic acid linker of the present invention (SEQ ID NOS 2, 1 and 13, respectively, in order of appearance).

In FIG. 1, Pu represents puromycin and ATCG represents a DNA sequence. In addition, Spc18 represents a spacer (first spacer) constituting an arm portion.

A nucleic acid linker 2 of the present embodiment comprises a spacer portion 51c at the 5'-terminal; a polynucleotide portion 51a hybridizable with at least a part of a sequence of mRNA 23 to be screened; and an arm portion 51b which has a connection portion 2a for the protein or peptide 33 at the 3'-terminal. In the nucleic acid linker 2 of the present embodiment, the spacer portion 51c, the polynucleotide portion 51a, and the arm portion 51b form a single strand in this order.

The polynucleotide portion 51a may be DNA or a nucleic acid derivative such as PNA (polynucleopeptide), and is preferably modified DNA to which nuclease resistance is provided.

As the modified DNA, any modified DNA, such as DNA having an internucleoside bond such as phosphorothioate, and DNA having sugar modification such as 2'-fluoro or 2'-O-alkyl, which is known in the technical art, may be used.

Moreover, the polynucleotide portion 51a comprises a photoreactive base derivative 2b. The photoreactive base derivative 2b means a base derivative in which reactivity is activated through irradiation with light of a predetermined wavelength and which can crosslink the nucleic acid linker 2 and the mRNA 23.

The photoreactive base derivative 2b preferably uses a reversible photo-coupling base. The reversible photo-coupling base contains a base which performs reversible photo-coupling and photo cleavage on the nucleic acid linker 2 and the mRNA 23 through irradiation with light in different wavelength bands. Examples of the reversible photo-coupling base include a base, to which psoralen is added, and 3-cyanovinylcarbazole nucleoside (hereinafter, also referred to as $^{CNV}$K).

It is necessary for the reversible photo-coupling base to be able to efficiently performing crosslinking in a short period of time; therefore, $^{CNV}$K preferable.

In a case of using $^{CNV}$K as the photoreactive base derivative 2b, it is possible to perform a crosslinking reaction by irradiating a complex of the nucleic acid linker 2 and the mRNA 23 with light in a first wavelength band for photocoupling and with light in a second wavelength band for photo cleavage. The light in the first wavelength band is light of greater than or equal to 340 nm. For example, a crosslinking structure is formed by an atom which constitutes $^{CNV}$K and an atom which constitutes a pyrimidine base in the mRNA 23 which forms a base pair with a purine base adjacent to $^{CNV}$K on the 5' side, through irradiation with light in a wavelength band of 340 nm to 380 nm. The second wavelength band is light of less than 350 nm. For example, the crosslinking is released through irradiation with light in a wavelength band of 280 nm to 345 nm. In the first wavelength band and the second wavelength band, parts of the first and the second wavelength bands may overlap each other.

With the use of $^{CNV}$K, it is possible to obtain high crosslinking efficiency through irradiation with light in a predetermined wavelength band over a short period of time (for example, 30 seconds). Therefore, there is no concern that a nucleic acid to be irradiated will be damaged. In addition, $^{CNV}$K is excellent in that it is possible to perform an efficient reversible crosslinking reaction.

The arm portion 51b functions as a spacer which holds the mRNA 23 and the connection portion 2a for a protein or a peptide at desired distances. The 5'-terminal of the arm portion 51b is bound to the 3'-terminal of the polynucleotide portion 51a and the 3'-terminal of the arm portion 51b has a protein connection portion 2a.

The arm portion 51b except for the 3'-terminal may be labeled with a marker. Examples of the marker include fluorescent pigments, fluorescent beads, quantum dots, biotin, antibodies, antigens, energy-absorbing substances, radioisotopes, chemical illuminants, and enzymes.

Examples of the fluorescent pigments include FAM (carboxyfluorescein), JOE (6-carboxy-4',5'-dichloro-2',7'-dimethoxy fluorescein), FITC (fluorescein isothiocyanate), TET (tetrachloro-fluorescein), HEX (5'-hexachloro-fluorescein-CE phosphoroamidite), Cy3, Cy5, Alexa 568, and Alexa 647.

There is a connection portion 2a for the protein or peptide 33 at the 3'-terminal of the arm portion 51b. The protein or peptide connection portion 2a means a structure which has characteristics of being specifically bound to the C-terminal of the protein or peptide 33 under elongation on a ribosome under predetermined conditions, and puromycin is a representative example thereof.

Puromycin is a protein synthesis inhibitor which has a structure similar to the 3'-terminal of aminoacyl-tRNA. An arbitrary substance can be used as the connection portion 2a for a protein 33 as long as the arbitrary substance has a function of being specifically bonded to the C-terminal of the protein or peptide 33 under elongation. Examples thereof include puromycin derivatives such as 3'-N-aminoacyl puromycin aminonucleoside (PANS-amino acid) and 3'-N-aminoacyl adenosine amino nucleoside (AANS-amino acid).

Examples of the PANS-amino acid include PANS-Gly of which the amino acid portion is glycine, PANS-Val of which the amino acid portion is valine, PANS-Ala of which the amino acid portion is alanine, or a PANS-amino acid mixture of which the amino acid portions correspond to each amino acid of all of the amino acids.

Examples of the AANS-amino acid include AANS-Gly of which the amino acid portion is glycine, AANS-Val of which the amino acid portion is valine, AANS-Ala of which the amino acid portion is alanine, and an AANS-amino acid mixture of which the amino acid portions correspond to all of the amino acids.

Examples of the aminoacyl-tRNA 3'-terminal analog which can be favorably used in addition to puromycin include ribocytidyl puromycin (rCpPur), deoxydyl puromycin (dCpPur), and deoxyuridyl puromycin (dUpPur).

The arm portion 51b may be constituted of a nucleic acid linker or a nucleic acid derivative or may be constituted of a polymer such as polyethylene glycol as long as the arm portion 51b functions as a spacer (first spacer). Modification for improving stability of puromycin or a label for detecting a complex may be further added to the arm portion 51b. In a case where the nucleic acid linker 2 of the present embodiment is used for an mRNA-nucleic acid linker-reverse transcription primer complex to be described later, the arm portion 51b preferably has a nucleic acid or a nucleic acid derivative for forming a complementary pair with a reverse transcription primer.

The nucleic acid linker 2 of the present embodiment has the spacer portion 51c (second spacer) at the 5'-terminal. The present inventors have found that the spacer portion 51c is required in order to efficiently produce the mRNA-nucleic acid linker-protein complex on a solid phase. In a step of synthesizing the protein or peptide 33, it is necessary to keep a predetermined distance from the solid phase in order to suppress inhibition of the synthesis of the protein or peptide 33 due to contact between ribosome and the solid phase. For this reason, the nucleic acid linker 2 of the present embodiment has the spacer portion 51c (second spacer) at the 5'-terminal and the spacer portion has a plurality of bases. For example, the spacer portion of the present embodiment has oligonucleotides with about 50 or more bases.

In addition, the spacer portion 51c preferably has a bonding site with the solid phase at the 5'-terminal.

In combining the solid phase bonding site and a solid phase bonding site recognition site on a solid phase which recognizes the solid phase bonding site, it is possible to use a method of modifying a nucleic acid linker 2 with a functional group such as an amino group, a formyl group, and an SH group and using a solid phase which is subjected to surface treatment using a silane coupling agent which has an amino group, a formyl group, and an epoxy group; or a method of using gold-thiol bonding, in addition to a method of using avidin-biotin bonding, with preference given to the method of using gold-thiol bonding.

The nucleic acid linker 2 of the present embodiment has a simple structure called a single strand. Therefore, it is possible to easily produce the nucleic acid linker of the present embodiment compared to a nucleic acid linker in the related art. For this reason, it is possible to rapidly and simply prepare a peptide or a protein using the nucleic acid linker.

Furthermore, the nucleic acid linker 2 of the present embodiment has the spacer portion 51c; therefore, it is suitable for synthesizing the protein or peptide 33 on a solid phase.

Furthermore, the nucleic acid linker 2 of the present embodiment contains the photoreactive base derivative 2b;

therefore, the complex with the mRNA 23 can be stabilized and the protein or peptide 33 can be efficiently synthesized.

Second Embodiment

The structure of the nucleic acid linker 12 of the present embodiment will be described using FIG. 2.

Figure 2:
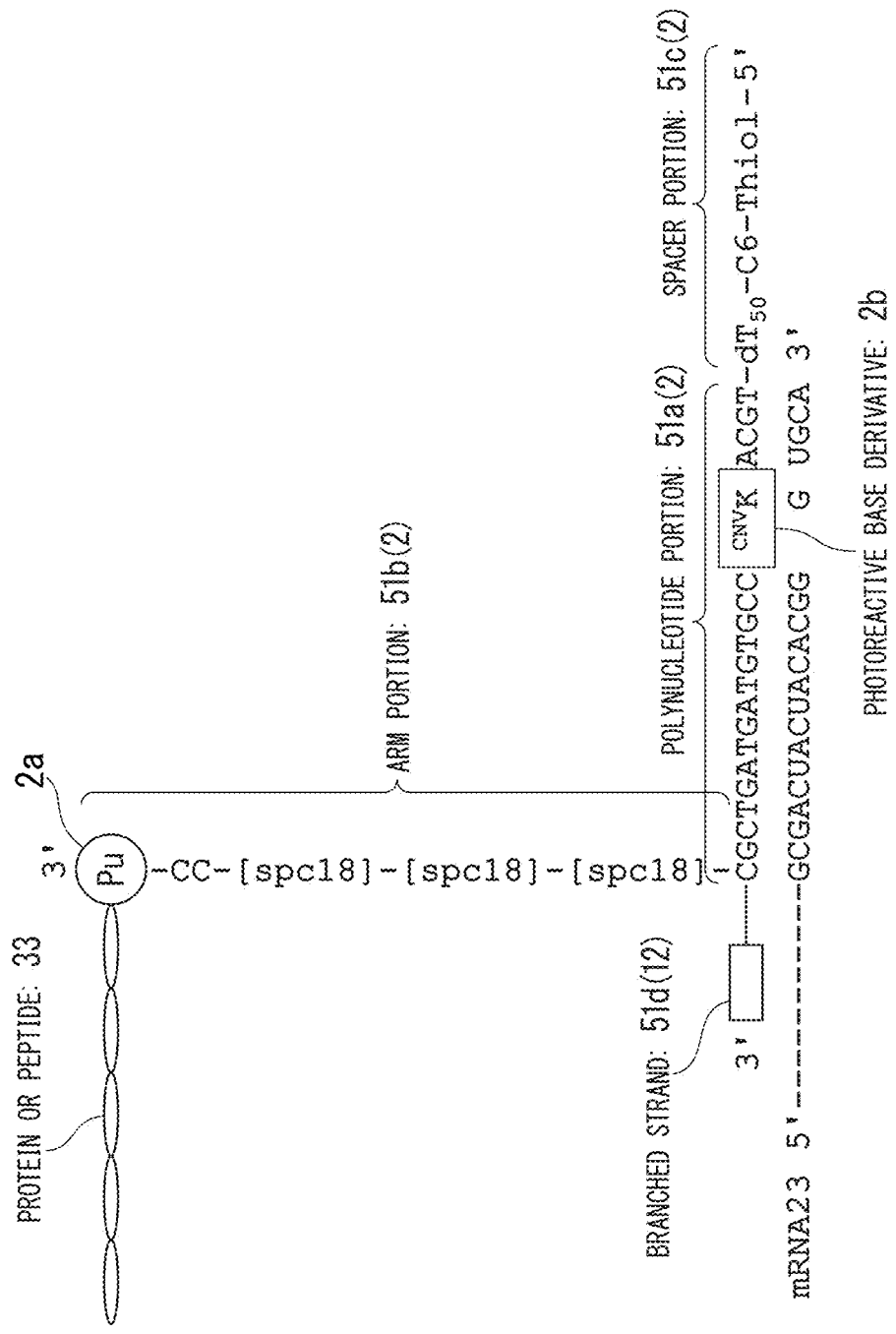
FIG. 2 is a view showing a mode of a nucleic acid linker of the present invention (SEQ ID NOS 2, 1 and 13, respectively, in order of appearance).

In FIG. 2, constituents the same as those shown in the schematic view of the nucleic acid linker 2 in FIG. 1 will be given the same reference numerals, and the description thereof will not be repeated.

Similarly to the first embodiment, a nucleic acid linker 12 of the present embodiment includes a spacer portion 51c at the 5'-terminal; a polynucleotide portion 51a hybridizable with at least a part of the sequence of the mRNA 23 to be screened; and an arm portion 51b which has a connection portion 2a for a protein or peptide 33 at the 3'-terminal. In the nucleic acid linker 12 of the present embodiment, the spacer portion 51c, the polynucleotide portion 51a, and the arm portion 51b form a single strand in this order. The nucleic acid linker 12 of the present embodiment further has a branched strand 51d which has the 3'-terminal protruding from the space between the polynucleotide portion 51a and the arm portion 51b. The branched strand 51d has a primer sequence which is hybridized with a part of a sequence of the mRNA 23 and reversely transcribes the mRNA 23.

The branched strand 51d forms a T-shaped structure by being bound with a single-stranded polynucleotide portion 51a at a position on the 5' side of a plurality of bases from the 3'-terminal of the branched strand 51d. The 3'-terminal of the branched strand 51d functions as a primer during the reverse transcription.

According to the nucleic acid linker 12 of the present embodiment, since it has the branched strand 51d, cDNA can be obtained which is produced by reversely transcribing mRNA that encodes a protein to be screened in addition to the effect of the first embodiment.

Nucleic Acid Linker-Reverse Transcription Primer Complex

First Embodiment

Figure 3:
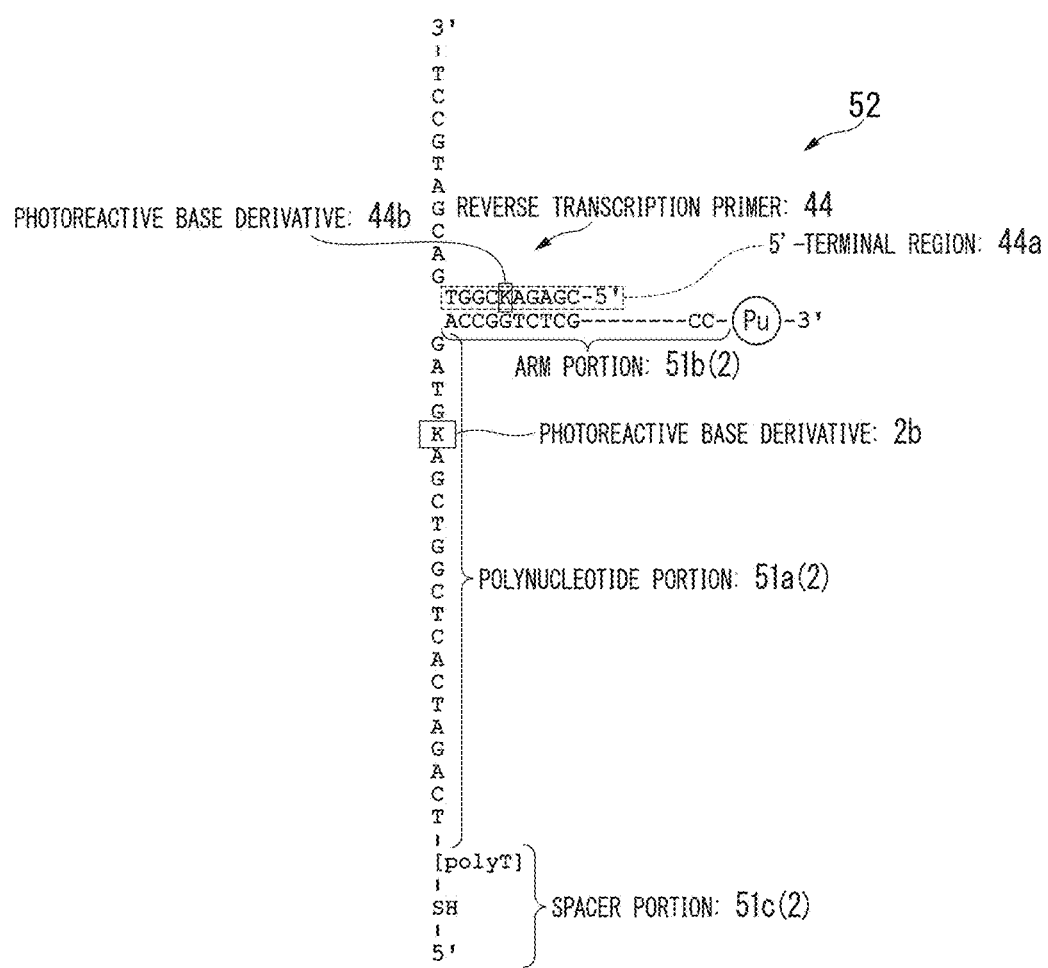
FIG. 3 is a view showing a mode of a nucleic acid linker-reverse transcription primer complex of the present invention (SEQ ID NOS 6, 5, 4 and 14, respectively, in order of appearance).

A nucleic acid linker-reverse transcription primer complex 52 of the present embodiment is a complex formed of the nucleic acid linker 2 and a reverse transcription primer 44 of mRNA. The structure of the nucleic acid linker-reverse transcription primer complex 52 (hereinafter, also referred to as a complex 52) of the present embodiment will be described using FIG. 3. In FIG. 3, constituents the same as those shown in the schematic view of the nucleic acid linker 2 in FIG. 1 will be given the same reference numerals, and the description thereof will not be repeated.

The reverse transcription primer 44 comprises a 5'-terminal region portion 44a having a sequence hybridizable with at least a part of a sequence of the arm portion 51b of the nucleic acid linker 2.

The nucleic acid linker 2 constituting the complex 52 of the present embodiment has the same configuration as that described above as the first embodiment of the nucleic acid linker. In the complex 52 of the present embodiment, the arm portion 51b of the nucleic acid linker 2 preferably has a nucleic acid or a nucleic acid derivative for forming a complementary pair with a reverse transcription primer.

The reverse transcription primer 44 forms a complementary pair with the arm portion 51b of the nucleic acid linker 2 through the 5'-terminal region 44a.

From the viewpoint of stabilizing the complex 52, the 5'-terminal region portion 44a in the reverse transcription primer 44 preferably comprises a photoreactive base derivative 44b. The photoreactive base derivative 44b preferably uses a reversible photo-coupling base. In the present embodiment, the photoreactive base derivative 44b uses $^{CNV}K$ since it is possible to perform an efficient reversible crosslinking reaction in a short period of time.

mRNA-Nucleic Acid Linker-Reverse Transcription Primer Complex

First Embodiment

Figure 4:
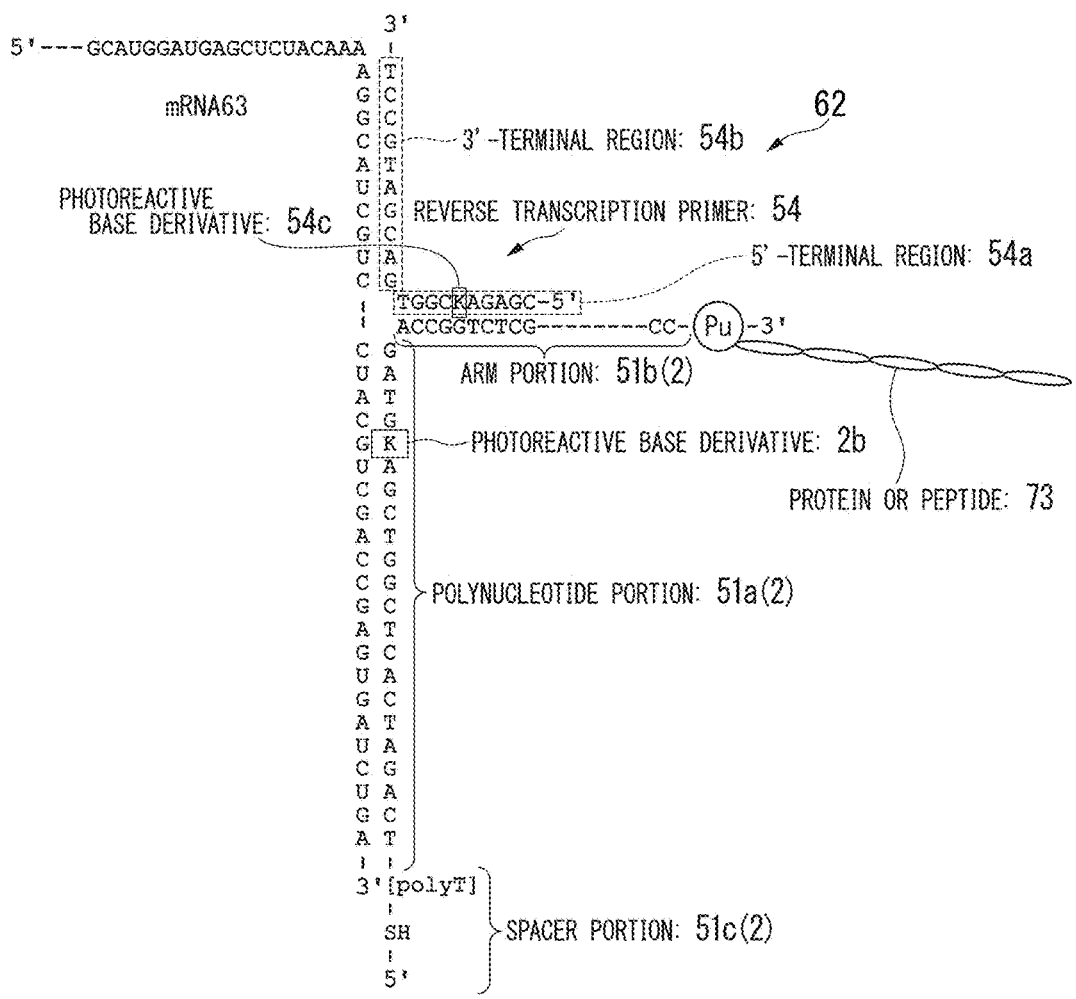
FIG. 4 is a view showing a mode of mRNA-nucleic acid linker-reverse transcription primer complex of the present invention (SEQ ID NOS 15, 6, 5, 4 and 14, respectively, in order of appearance).

An mRNA-nucleic acid linker-reverse transcription primer complex 62 of the present embodiment is a complex formed of the nucleic acid linker 2, mRNA 63, and a reverse transcription primer 54 of the mRNA 63. The structure of the mRNA-nucleic acid linker-reverse transcription primer complex 62 (hereinafter, also referred to as a complex 62) of the present embodiment will be described using FIG. 4. In FIG. 4, constituents the same as those shown in the schematic view of the nucleic acid linker 2 in FIGS. 1 and 3 will be given the same reference numerals, and the description thereof will not be repeated.

The reverse transcription primer 54 is formed of a 5'-terminal region portion 54a having a sequence hybridizable with at least a part of the sequence of the arm portion 51b of the nucleic acid linker 2 and a 3'-terminal region portion 54b hybridizable with at least a part of a sequence of the mRNA 63.

The reverse transcription primer 54 forms a complementary pair with the arm portion 51b of the nucleic acid linker 2 through the 5'-terminal region 54a. In addition, the reverse transcription primer 54 forms a complementary pair with the mRNA 63 through the 3'-terminal region 54b.

The nucleic acid linker 2 forms a complementary pair with the mRNA 63 through the polynucleotide portion 51a and forms a complementary pair with the reverse transcription primer 54 through the arm portion 51b.

Three nucleic acid strands of the reverse transcription primer 54, the nucleic acid linker 2, and the mRNA 63 form a double strand together such that the complex 62 of the present embodiment forms a structure in which three double-stranded nucleic acids intersect at one site. In addition, three nucleic acid strands of the reverse transcription primer 54, the nucleic acid linker 2, and the mRNA 63 form a double strand together such that the complex 62 of the present embodiment forms a structure in which three double-stranded nucleic acids extend in a direction different from each other at a common region as a base point.

From the viewpoint of stabilizing the complex 62, the 5'-terminal region portion 54a in the reverse transcription primer 54 preferably comprises a photoreactive base derivative 54c. The photoreactive base derivative 54c preferably uses a reversible photo-coupling base. In the present embodiment, the photoreactive base derivative 54c uses $^{CNV}K$ since it is possible to perform an efficient crosslinking reaction in a short period of time.

The complex 62 of the present embodiment exhibits the same effect as that of the first embodiment of the above-described nucleic acid linker, and therefore, it is possible to rapidly, simply, and efficiently synthesize a peptide or a protein.

In addition, the complex 62 of the present embodiment exhibits the same effect as that of the second embodiment of the above-described nucleic acid linker, and therefore, it is possible to obtain cDNA which is produced by reversely transcribing mRNA encoding a protein to be screened.

Furthermore, the complex 62 of the present embodiment is favorably used for the method of recovering a nucleic acid which encodes a protein or a peptide to be screened. Hereinafter, it is explained with reference to preferable embodiments <<Nucleic Acid Linker-Immobilized Solid Phase>>

The nucleic acid linker-immobilized solid phase of the present embodiment is obtained such that the nucleic acid linker of the above-described embodiment is immobilized on the solid phase. Examples of the solid phase include a substrate or a carrier.

First Embodiment

The nucleic acid linker-immobilized solid phase of the present embodiment is obtained such that the above-described nucleic acid linker of the embodiment is immobilized on a substrate.

Examples of the substrate include a glass substrate, a silicon substrate, a plastic substrate, and a metallic substrate. As described above, the nucleic acid linker of the present embodiment has a spacer portion. It is preferable that the spacer portion have a bonding site with the solid phase at the 5'-terminal. The nucleic acid linker is immobilized on a substrate through bonding of a solid phase bonding site and a solid phase bonding site recognition site which is bound to the substrate.

As such combination of the solid phase bonding site and the solid phase bonding site recognition site, gold-thiol bonding is preferably used as described above. From such a viewpoint, a metallic substrate is preferable as the substrate.

In a case of using a metallic substrate as the substrate, it is preferable that the metallic substrate be first subjected to SPM washing (sulfuric acid hydrogen peroxide solution) to remove an organic substance on the metallic substrate through an oxidative action. Next, it is preferable that a nucleic acid linker having thiol, which is a bonding site with the solid phase at the 5'-terminal, be dripped on the metallic substrate and be reacted in a closed space at room temperature for 20 hours to 24 hours, and then, reactions other than the gold-thiol bonding on the metallic substrate are blocked using a reducing agent.

As the reducing agent, 6-mercapto-1-hexanol is preferably used. The metallic substrate on which the nucleic acid linker is efficiently spotted is obtained through the blocking treatment.

Second Embodiment

The nucleic acid linker-immobilized solid phase of the present embodiment is obtained such that the nucleic acid linker of the above-described embodiment is immobilized on a beads carrier.

Examples of the beads carrier include magnetic beads, gold nanoparticles, agarose beads, and plastic beads, and magnetic beads are preferable due to easy handling using magnetism. It is possible to constitute a nucleic acid linker-immobilized array by sequencing the nucleic acid-immobilized beads in a reaction tank in a substrate for a beads device in which a plurality of reaction tanks are provided. Examples of the method of immobilizing a nucleic acid linker include, in addition to the above-described method of using avidin-biotin bonding, a method of modifying a nucleic acid linker with a functional group such as an amino group, a formyl group, and an SH group and using a beads carrier which is subjected to surface treatment using a silane coupling agent which has an amino group, a formyl group, and an epoxy group. Particularly, the method of using avidin-biotin bonding is preferable.

Nucleic Acid Linker-Reverse Transcription Primer Complex-Immobilized Solid Phase First Embodiment The nucleic acid linker-reverse transcription primer complex-immobilized solid phase of the present embodiment is obtained such that the above-described nucleic acid linker-reverse transcription primer complex of the first embodiment is immobilized on the solid phase. Similarly to the <<Nucleic Acid Linker-immobilized Solid Phase>>, examples of the solid phase include a substrate or a carrier.

Protein- or Peptide-Immobilized Solid Phase

First Embodiment

The protein- or peptide-immobilized solid phase of the present embodiment is obtained such that the mRNA 23, the above-described nucleic acid linker 2 of the first embodiment, and a complex of a protein or peptide 33 which is encoded by the mRNA 23 are immobilized on the solid phase (refer to FIG. 1). Similarly to the <<Nucleic Acid Linker-immobilized Solid Phase>>, examples of the solid phase include a substrate or a carrier.

The protein- or peptide-immobilized solid phase of the present embodiment is produced using the above-described nucleic acid linker-immobilized solid phase which is obtained such that the nucleic acid linker 2 is immobilized on the solid phase.

That is, a method of producing a protein- or peptide-immobilized solid phase of the present embodiment comprises: (a) bringing mRNA 23 into contact with the nucleic acid linker-immobilized solid phase of the present embodiment to hybridize the mRNA 23 with the nucleic acid linker 2 to form an mRNA 23-nucleic acid linker 2 complex on the solid phase; (b) irradiating the mRNA 23-nucleic acid linker 2 complex on the solid phase with light in a first wavelength band after the (a) to crosslink the nucleic acid linker 2 and the mRNA 23; and (c) synthesizing a protein or peptide 33 from the mRNA 23 using a cell-free protein translation system after the (b) and bonding the C-terminal of the protein or peptide 33 to the connection portion 2a for the protein or the peptide of the nucleic acid linker 2, to produce an mRNA-nucleic acid linker-protein or peptide complex on the solid phase.

Hereinafter, each of the operations (a) to (c) will be described.

In the (a), the mRNA 23 is hybridized with the nucleic acid linker 2. First, preparation of the mRNA which is used in the (a) will be described.

The mRNA 23 is obtained by preparing DNA which encodes a protein or a peptide to be screened and transcribing the prepared DNA using RNA polymerase. Examples of the RNA polymerase include T7 RNA polymerase.

As the DNA, it is possible to use arbitrary DNA or an arbitrary DNA library. For example, it is possible to use cDNA library which is obtained from a sample tissue, a DNA library in which the sequence is randomly synthesized, a DNA library in which a part of the sequence is mutated, and the like.

For easy purification of a protein or a peptide to be produced, it is preferable that a base sequence which encodes a tag such as polyhistidine or FLAG be added to a terminal of DNA in advance through PCR or the like. In addition, in order to improve the transcription efficiency, it is preferable that a T7 promoter sequence be added to the 5'-terminal of DNA in advance through PCR or the like. Moreover, in order to improve the translation efficiency, it is preferable that an omega sequence be added to the 5'-terminal of DNA in advance through PCR or the like.

Next, the 3'-terminal region of mRNA 23 is hybridized with the 5'-terminal region of the nucleic acid linker 2. For example, the mRNA 23 is heated to 90° C. and is denatured, and is then cooled to 25° C. over one hour to reliably hybridize the mRNA 23 with the nucleic acid linker 2.

Next, in the (b), the mRNA 23-nucleic acid linker 2 complex on the solid phase is irradiated with light in a first wavelength band after the (a) to crosslink the nucleic acid linker 2 and the mRNA 23.

The light in the first wavelength band is light of greater than or equal to 340 nm. For example, irradiation with light in a wavelength band of 340 nm to 380 nm is performed. The irradiation time may be short in view of suppressing damage to the nucleic acid due to irradiation, and is preferably 5 seconds to 60 seconds. In addition, the irradiation time is more preferably 10 seconds to 50 seconds, and particularly preferably 20 seconds to 40 seconds. For example, 60% or more of an mRNA 23-nucleic acid linker 2 complex formation rate with respect to the total number of moles of the mRNA 23 and the nucleic acid linker 2 is obtained through irradiation with light of 365 nm for 30 seconds.

A buffer which is used when performing the crosslinking reaction is not particularly limited and examples thereof include a Tris-HCL buffer. As a salt in the buffer, 100 mM to 1 M of NaCl is preferable and 200 mM to 600 mM of NaCl is more preferable. For example, 80% or more of an mRNA 23-nucleic acid linker 2 complex formation rate is obtained by the salt in the buffer being 200 mM of NaCl.

Furthermore, after the crosslinking reaction, it is preferable that the solid phase be washed in view of removing remaining mRNA which is not crosslinked. The washing method is not particularly limited and examples thereof include a method which is known in the related art. For example, a method of denaturing mRNA which is not crosslinked for removal using 8 M of a urea-containing buffer is preferable.

Next, in the (c), a protein or peptide 33 is synthesized from the mRNA 23 using a cell-free protein translation system after the (b).

The cell-free protein translation system is a protein translation system which is formed of components having an ability of synthesizing a protein which is extracted from an appropriate cell. The system includes elements, such as ribosome, translation initiation factors, translation elongation factors, dissociation factors, and aminoacyl tRNA synthetase, which are required for translation. Examples of such a protein translation system include *E. coli* extracts, rabbit reticulocyte extracts, and wheat germ extracts. In the present embodiment, the rabbit reticulocyte extracts are preferable in terms of suppressing the decomposition of mRNA.

Furthermore, there is an example of a reconstituted cell-free protein synthesis system which is formed of only factors in which elements required for translation are independently purified. The reconfiguration type cell-free protein synthesis system can more easily prevent nuclease or protease from being mixed in comparison to a case of using a cell extract in the related art. Therefore, it is possible to improve the translation efficiency.

With the use of such a system, the mRNA-nucleic acid linker-protein complex or the mRNA-nucleic acid linker-peptide complex is produced on the solid phase.

Second Embodiment

In the protein- or peptide-immobilized solid phase of the present embodiment, the complex of the mRNA 23, the above-described nucleic acid linker 12, and a protein or peptide 33 which is encoded by the mRNA 23 is immobilized on the solid phase (refer to FIG. 2). Similarly to the <<Nucleic Acid Linker-immobilized Solid Phase>>, examples of the solid phase include a substrate or a carrier.

The protein- or peptide-immobilized solid phase of the present embodiment is the same as that of the first embodiment except for the use of nucleic acid linker 12. Therefore, the description thereof will not be repeated.

Third Embodiment

The protein- or peptide-immobilized solid phase of the present embodiment is obtained such that the above-described mRNA 63-nucleic acid linker 2-reverse transcription primer 54 complex and an mRNA 23-nucleic acid linker 2-protein or peptide 73-reverse transcription primer 54-complex which is a complex of a protein or peptide 73 which is encoded by the mRNA 63 are immobilized on the solid phase (refer to FIG. 4).

Similarly to the <<Nucleic Acid Linker-immobilized Solid Phase>>, examples of the solid phase include a substrate or a carrier.

From the viewpoint of stabilizing the complex 62, the 5'-terminal region portion 54a in the reverse transcription primer 54 preferably comprises a photoreactive base derivative 54c. The photoreactive base derivative 54c preferably uses a reversible photo-coupling base. In the present embodiment, the photoreactive base derivative 54c uses $^{CNV}K$ since it is possible to perform an efficient reversible crosslinking reaction in a short period of time. The method of producing a protein- or peptide-immobilized solid phase of the present embodiment comprises: (a') bringing mRNA 63 and a reverse transcription primer 54 brought into contact with the nucleic acid linker-immobilized solid phase of the present embodiment and forming a double strands of three nucleic acid strands of the reverse transcription primer 54, the nucleic acid linker 2, and the mRNA 63 such that an mRNA 63-nucleic acid linker 2-reverse transcription primer 54 complex is formed on the solid phase; (b') irradiating the mRNA 63-nucleic acid linker 2-reverse transcription primer 54 complex on the solid phase with light in a first wavelength band after the (a')), and crosslinking the nucleic acid linker 2 and the mRNA 63 and crosslinking the nucleic acid linker 2 and the reverse transcription primer 54; and (c') synthesizing a protein or peptide 73 from the mRNA 63 using a cell-free protein translation system after the (b') and bonding the C-terminal of the protein or peptide 73 to the connection portion 2a for the protein or the peptide of the nucleic acid linker 2, to produce an mRNA-nucleic acid linker-protein- or peptide-reverse transcription primer complex on the solid phase.

Hereinafter, each of the operations (a') to (c') will be described.

In the (a'), the mRNA 63 and the reverse transcription primer 54 are hybridized with the nucleic acid linker 2. The order in which each molecule is hybridized with the nucleic acid linker is not particularly limited. The mRNA 63-nucleic acid linker 2-reverse transcription primer 54 complex may be formed by adding the reverse transcription primer 54 to the system after an mRNA 63-nucleic acid linker 2 complex is formed. The mRNA 63-nucleic acid linker 2-reverse transcription primer 54 complex may be formed by adding the mRNA 63 to the system after a nucleic acid linker 2-reverse transcription primer 54-complex is formed. In addition, the mRNA 63-nucleic acid linker 2-reverse transcription primer 54 complex may be formed by adding an mRNA 63-reverse transcription primer 54 complex, which has been previously formed, to the system.

Next, in the (b'), the mRNA 63-nucleic acid linker 2-reverse transcription primer 54 on the solid phase is irradiated with light in a first wavelength band after the (a') to crosslink the nucleic acid linker 2 and the mRNA 63 and to crosslink the nucleic acid linker 2 and the reverse transcription primer 54. The light in the first wavelength band is light of greater than or equal to 340 nm. For example, irradiation with light in a wavelength band of 340 nm to 380 nm is performed. The irradiation time may be short in view of suppressing damage to the nucleic acid due to irradiation, and is preferably 5 seconds to 60 seconds. In addition, the irradiation time is more preferably 10 seconds to 50 seconds, and particularly preferably 20 seconds to 40 seconds. The structure in which three double-stranded nucleic acids intersect at one site is stabilized by crosslinking two sites in the mRNA 63-nucleic acid linker 2-reverse transcription primer 54 complex.

Next, in the (c'), a protein or peptide 33 is synthesized from the mRNA 63 using a cell-free protein translation system after the (b'). The (c') is the same as the (c) except that the produced complex is the mRNA-nucleic acid linker-protein- or peptide-reverse transcription primer complex. Therefore, the description thereof will not be repeated.

<<Microarray>>

In a microarray of the present embodiment, a plurality of nucleic acid linkers, a plurality of nucleic acid linker-reverse transcription primer complexes, or a plurality of mRNA-nucleic acid linker-protein complexes are immobilized. The nucleic acid linker, the nucleic acid linker-reverse transcription primer complex, and the mRNA-nucleic acid linker-protein complex are described above in each embodiment. Therefore, the description thereof will not be repeated.

<<Nucleic Acid Recovery Method 1>>

The nucleic acid recovery method of the present embodiment is a nucleic acid recovery method, in which a nucleic acid is recovered using a solid phase on which the nucleic acid linker of the present embodiment is immobilized, and which comprises (A1) photocrosslinking the mRNA and the nucleic acid linker using a photoreactive base derivative; and (B1) dissociating the photocrosslinking of the mRNA and the nucleic acid through light irradiation.

The (A1) preferably comprises crosslinking a nucleic acid linker and mRNA through irradiation with light in a first wavelength band.

In addition, the (B1) preferably comprises dissociating the mRNA from the nucleic acid linker through irradiation with light in a second wavelength band.

Hereinafter, preferred embodiments will be described.

First Embodiment

Figure 5:
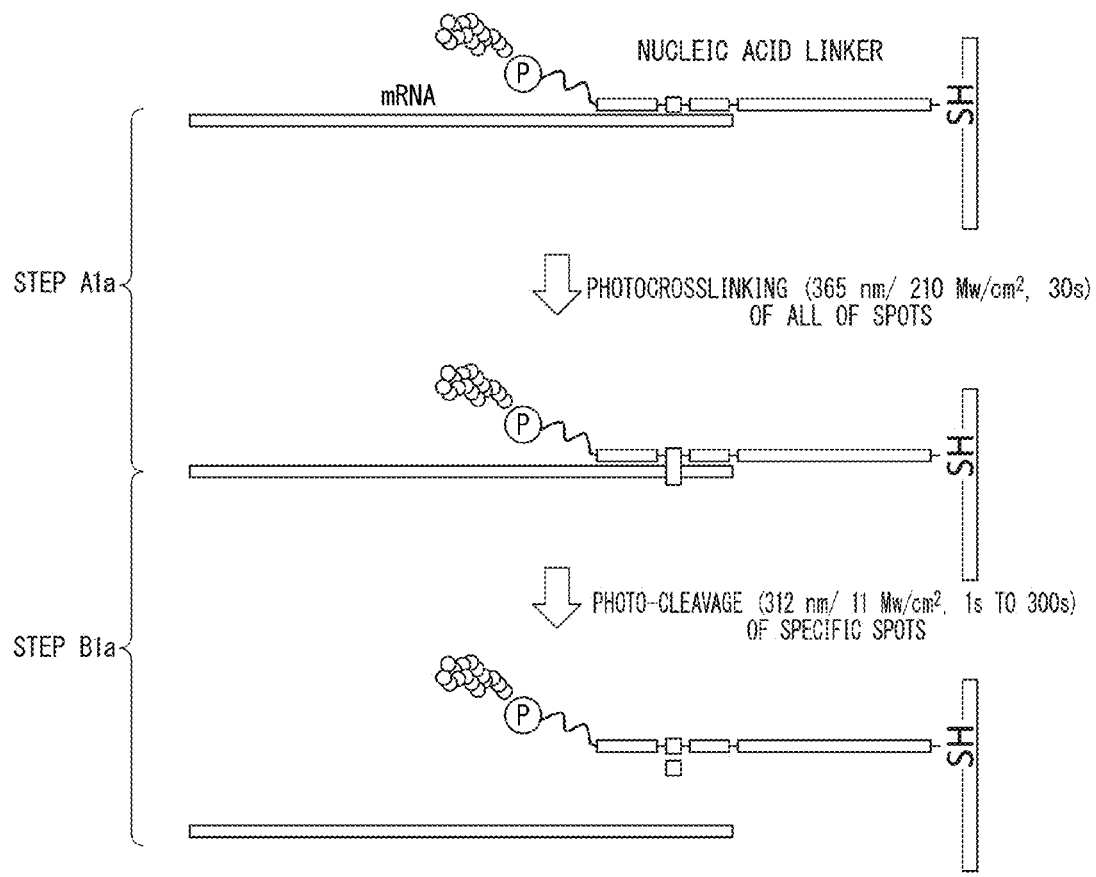
FIG. 5 is a view showing a mode of a nucleic acid recovery method of the present invention.

The nucleic acid recovery method of the present embodiment comprises:

(A1a) of irradiating all spots on a solid phase, on which nucleic acid linkers of the first embodiment or the second embodiment are immobilized, with light in a first wavelength band to crosslink mRNAs and the nucleic acid linkers in all of the spots; and (B1a) irradiating a specific spot on the solid phase with light in a second wavelength band to dissociate mRNA from a nucleic acid linker in the specific spot (refer to FIG. 5).

The nucleic acid recovery method of the present embodiment uses a photoreactive base derivative which is contained in the nucleic acid. As described above, it is possible to control the crosslinking reaction due to the wavelength band of the light with which the photoreactive base derivative is irradiated. In order to perform the crosslinking and the dissociating of a nucleic acid using a reversible photoreaction, a reversible photo-coupling base is preferably used as the photoreactive base derivative. Particularly, $^{CNV}K$ is preferably used as the photoreactive base derivative since it is possible to rigidly and efficiently perform the control.

The (A1a) corresponds to the (b) in the first embodiment of <<Protein- or Peptide-immobilized Solid Phase>>. The light in the first wavelength band is light of greater than or equal to 340 nm, and examples thereof include light of 340 nm to 380 nm. The irradiation time may be short in view of suppressing damage to the nucleic acid due to irradiation, and is preferably 5 seconds to 60 seconds. In addition, the irradiation time is more preferably 10 seconds to 50 seconds, and particularly preferably 20 seconds to 40 seconds. The nucleic acid linkers in all of the spots and the mRNAs are cross-linked through the (A1a). The formation of the nucleic acid linker-mRNA complex is maintained through the crosslinking reaction even if, for example, the solid phase is washed using a urea-containing buffer.

In the (B1a), the crosslinking which is formed in the (A1a) is released through irradiation with light in a second wavelength band which is different from that in a first wavelength band. The light in a second wavelength band is light of less than 350 nm, and examples thereof include light of 280 nm to 345 nm. In addition, the irradiation time may be short in view of suppressing damage to the nucleic acid due to irradiation, and is preferably 1 second to 300 seconds.

In addition, in the (B1a), a specific spot on the solid phase is selectively irradiated with light in a second wavelength band. As the selective light irradiation method, a method used in producing an array, for example, a method of using a mask, or the like is applied. mRNA of which the crosslinking is released is dissociated from the nucleic acid linker through a conventional method such as elution through heat treatment or using a urea-containing buffer. According to the nucleic acid recovery method of the present embodiment, it is possible to selectively recover the mRNA which is dissociated through irradiation with light in a second wavelength band.

Second Embodiment

Figure 6:
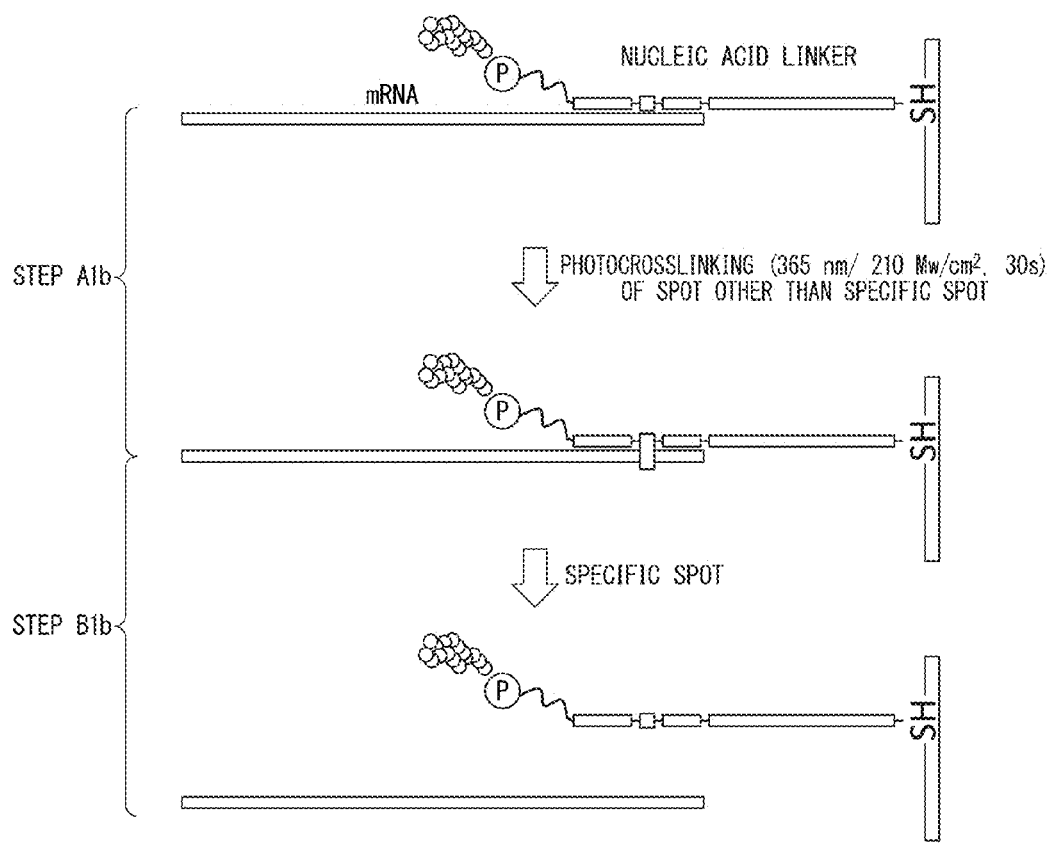
FIG. 6 is a view showing a mode of a nucleic acid recovery method of the present invention.

The nucleic acid recovery method of the present embodiment comprises:

(A1b) irradiating a spot other than the specific spot on a solid phase, on which a nucleic acid linker of the first embodiment or the second embodiment is immobilized, with light in a first wavelength band (greater than or equal to 340 nm; for example, 340 nm to 380 nm) to crosslink mRNA and the nucleic acid linker in the spot other than the specific spot; and (B1b) dissociating mRNA from a nucleic acid linker in the specific spot on the solid phase (refer to FIG. 6).

In the present embodiment, in the (A1b), the spot other than the specific spot on the solid phase is selectively irradiated with light in a first wavelength band, and the nucleic acid linker and the mRNA are crosslinked. Next, in the (B1b), the mRNA is dissociated from a nucleic acid linker in a spot which is not irradiated with light in a first wavelength band. The dissociation method is the same as that in the first embodiment. According to the nucleic acid recovery method of the present embodiment, it is possible to selectively recover the mRNA which is not irradiated with light in a first wavelength band.

<<Nucleic Acid Recovery Method 2>>

The nucleic acid recovery method of the present embodiment is a nucleic acid recovery method in which a nucleic acid is recovered using a solid phase on which the mRNA-nucleic acid linker-reverse transcription primer complex of the first embodiment is immobilized, the method comprising:

(A2) photocrosslinking the reverse transcription primer of the mRNA and the nucleic acid linker using a photoreactive base derivative; and (B2) dissociating the photocrosslinking of the reverse transcription primer and the nucleic acid linker through light irradiation.

The (A2) preferably comprises synthesizing cDNA which is obtained such that a complementary strand of the mRNA is elongated from the 3'-terminal of the reverse transcription primer by subjecting the mRNA-nucleic acid linker-reverse transcription primer complex to a reverse transcription reaction. Any reverse transcriptase well known in the related art is used as reverse transcriptase which is used for reverse transcription, and examples thereof include reverse transcriptase derived from Moloney Murine Leukemia virus.

The reverse-transcribed cDNA forms a hybrid of the mRNA in the mRNA-nucleic acid linker-protein or peptide complex. There is a high possibility that the mRNA in the mRNA-nucleic acid linker-protein or peptide complex may non-specifically interact with other components as an aptamer. Therefore, it is preferable to produce such an mRNA/cDNA-nucleic acid linker-protein or peptide complex.

In addition, it is necessary to produce the complex in order to analyze cDNA which encodes a protein or a peptide.

The cDNA is synthesized by elongating a complementary strand from the 3'-terminal of the reverse transcription primer which is hybridized with a nucleic acid linker. Accordingly, in the present embodiment, the cDNA individually exists without being integrated with the nucleic acid linker. The synthesized cDNA can be separated from the nucleic acid linker, and therefore, the nucleic acid recovery method of the present embodiment is suitable for the method of recovering cDNA.

Hereinafter, preferred embodiments of the nucleic acid recovery method will be described.

First Embodiment

The nucleic acid recovery method of the present embodiment comprises:

the (A2) of irradiating all spots on a solid phase with light to crosslink mRNA and nucleic acid linkers in all of the spots and the (B2) of dissociating a reverse transcription primer from a nucleic acid linker in a specific spot on the solid phase.

Figure 7:
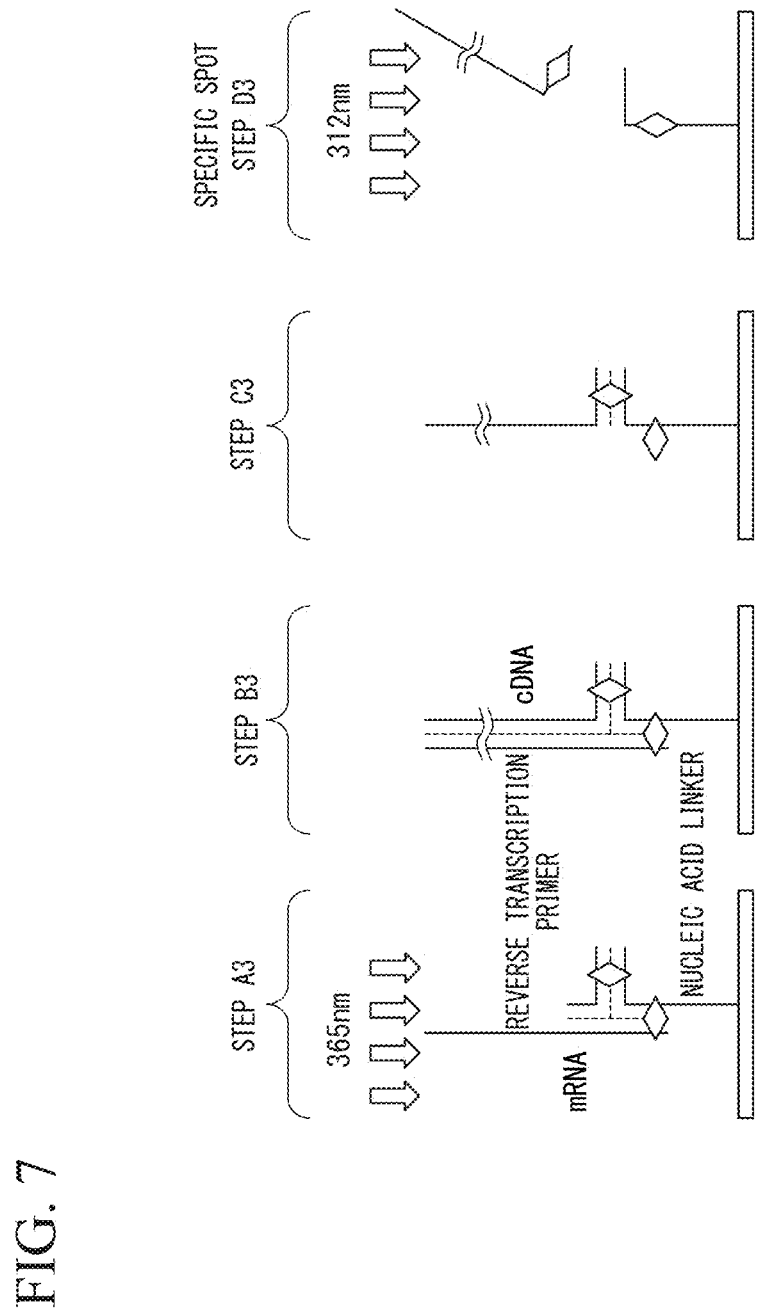
FIG. 7 is a view showing a mode of a nucleic acid recovery method of the present invention.

As shown in FIG. 7, the nucleic acid recovery method of the present embodiment specifically comprises:

(A3) irradiating all spots on an mRNA-nucleic acid linker-reverse transcription primer complex-immobilized solid phase with light in a first wavelength band to crosslink a nucleic acid linker and mRNA and to crosslink the nucleic acid linker and a reverse transcription primer;

(B3) synthesizing cDNA which is obtained such that a complementary strand is elongated from the 3'-terminal of the reverse transcription primer by subjecting the mRNA-nucleic acid linker-protein- or peptide-reverse transcription primer complex to a reverse transcription reaction to produce an mRNA/cDNA-nucleic acid linker-protein or peptide complex;

(C3) dissociating the mRNA from the mRNA/cDNA-nucleic acid linker-protein or peptide complex to produce a cDNA-nucleic acid linker-protein or peptide complex; and (D3) irradiating a specific spot on a protein- or peptide-immobilized solid phase with light in a second wavelength band to dissociate the cDNA from the cDNA-nucleic acid linker-protein or peptide complex in the specific spot.

In the (A3), the light in a first wavelength band is light of greater than or equal to 340 nm, and examples thereof include light of 340 nm to 380 nm. In addition, the irradiation time may be short in view of suppressing damage to the nucleic acid due to irradiation, and is preferably 5 seconds to 60 seconds, more preferably 10 seconds to 50 seconds, and particularly preferably 20 seconds to 40 seconds. mRNA and nucleic acid linker in all spots are crosslinked through the (A3).

The (B3) is producing mRNA/cDNA-nucleic acid linker-protein or peptide complex from mRNA-nucleic acid linker-protein- or peptide-reverse transcription primer complex through the above-described reverse transcription reaction.

The order of the (A3) and the (B3) are not particularly limited, and the order may be a crosslinking reaction→a reverse transcription reaction or may be a reverse transcription reaction→a crosslinking reaction.

In the (C3), the mRNA is dissociated from the mRNA/cDNA-nucleic acid linker-protein or peptide complex. This is because it is necessary to first dissociate mRNA which forms a complementary strand in order to recover the cDNA. The dissociation method is not particularly limited, and examples thereof include a dissociation method using heat or a denaturing agent or a dissociation method through decomposition of mRNA using RNase or an alkaline solution.

In the (D3), the crosslinking formed in the (A3) is released through irradiation light in a second wavelength band which is different from a first wavelength band. The light in a second wavelength band is light of less than 350 nm, and examples thereof include light of 280 nm to 345 nm. In addition, the irradiation time may be short in view of suppressing damage to the nucleic acid due to irradiation, and is preferably 1 second to 300 seconds.

In addition, in the (D3), a specific spot on a solid phase is selectively irradiated with light in a second wavelength band. As the method of selectively irradiating light, a method used in producing an array, for example, a method of using a mask, or the like is applied. cDNA of which the crosslinking is released is dissociated from the nucleic acid linker through a conventional method such as elution through heat treatment or using a urea-containing buffer. According to the nucleic acid recovery method of the present embodiment, it is possible to selectively recover the cDNA which is dissociated through irradiation with light in a second wavelength band.

Second Embodiment

The nucleic acid recovery method of the present embodiment comprises:

the (A2) of irradiating a spot other than a specific spot on a solid phase with light to crosslink a reverse transcription primer and a nucleic acid linker in the spot other than the specific spot; and the (B2) of dissociating the reverse transcription primer from the nucleic acid linker in the specific spot on the solid phase.

Figure 8:
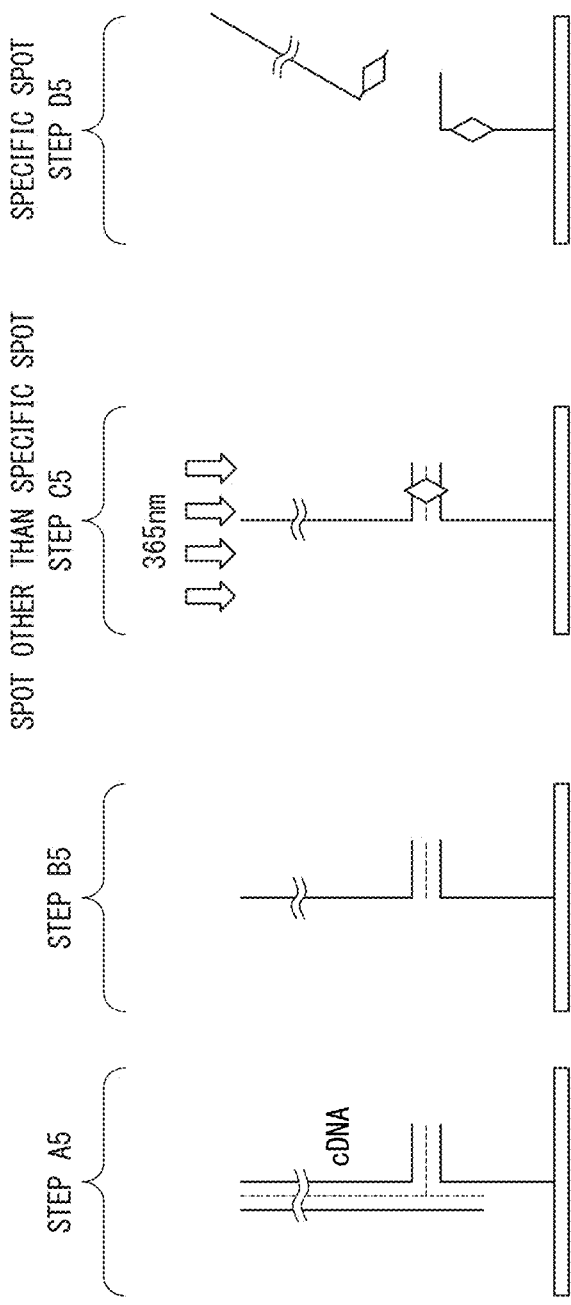
FIG. 8 is a view showing a mode of a nucleic acid recovery method of the present invention.

As shown in FIG. 8, the nucleic acid recovery method of the present embodiment specifically comprises:

(A5) synthesizing cDNA which is obtained such that a complementary strand is elongated from the 3'-terminal of the reverse transcription primer by subjecting an mRNA-nucleic acid linker-reverse transcription primer complex to a reverse transcription reaction, to produce an mRNA/cDNA-nucleic acid linker complex;

(B5) dissociating the mRNA in the mRNA/cDNA-nucleic acid linker complex from the mRNA/cDNA-nucleic acid linker complex to produce a cDNA-nucleic acid linker-protein or peptide complex;

(C5) irradiating a spot other than a specific spot on a solid phase with light in a first wavelength band to crosslink cDNA and a nucleic acid linker in the spot other than the specific spot; and (D5) dissociating the cDNA from the cDNA-nucleic acid linker-protein or peptide complex in the specific spot.

The operations (A5) to (C5) are the same as the operations in the first embodiment, and therefore, the description thereof will not be repeated. The order of the (B5) and the (C5) is not particularly limited, and the order may be an RNA dissociation reaction→a crosslinking reaction or may be a crosslinking reaction→an RNA dissociation reaction.

In the present embodiment, in the (C5), the spot other than the specific spot on the solid phase is selectively irradiated with light in a first wavelength band and the cDNA and the nucleic acid linker are crosslinked. Next, in the (D5), the cDNA is dissociated from a nucleic acid linker in a spot which is not irradiated with light in a first wavelength band. The dissociation method is the same as that in the first embodiment. According to the nucleic acid recovery method of the present embodiment, it is possible to selectively recover the mRNA which is not irradiated with light in a first wavelength band.

Method of Identifying Functional Protein

First Embodiment

Figure 9:
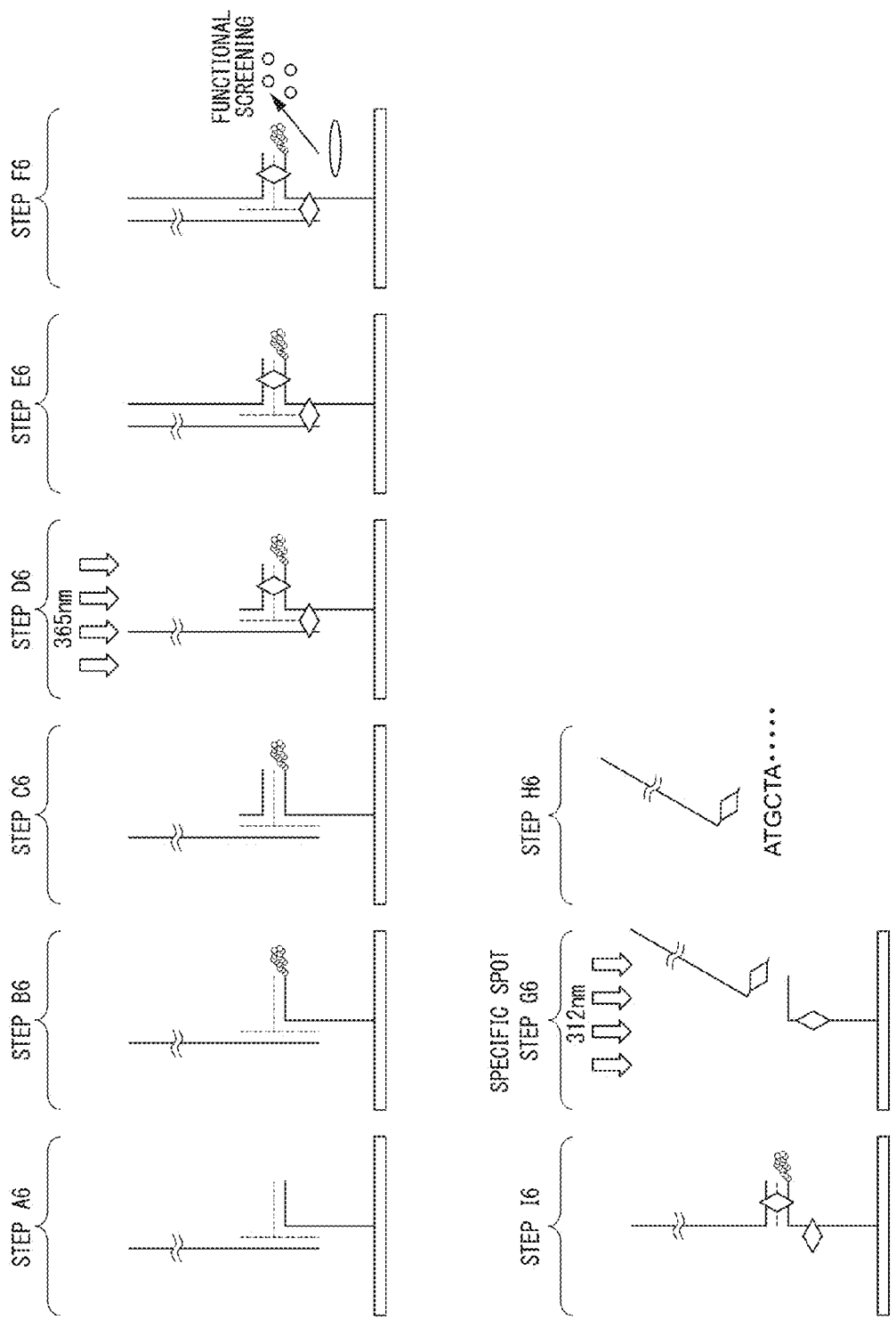
FIG. 9 is a view showing a mode of method of identifying a functional protein or a functional peptide of the present invention.

As shown in FIG. 9, a method of identifying a functional protein of the present embodiment comprises:

(A6) bringing mRNA into contact with a nucleic acid linker-immobilized solid phase of the present embodiment and hybridizing the mRNA with the nucleic acid linker to form an mRNA-nucleic acid linker complex on the solid phase;

(B6) synthesizing a protein or a peptide from the mRNA using a cell-free protein translation system and bonding the C-terminal of the protein or the peptide to a connection portion for the protein or the peptide to form an mRNA-nucleic acid linker-protein or peptide complex;

(C6) bringing a reverse transcription primer, which is formed of a 5'-terminal region portion having a sequence hybridizable with at least a part of a sequence of an arm portion of the nucleic acid linker, and contains 3-cyanovinylcarbazole nucleoside, and a 3'-terminal region portion having a sequence hybridizable with at least a part of a sequence of the mRNA, into contact with the solid phase to form an mRNA-nucleic acid linker-protein- or peptide-reverse transcription primer complex;

(D6)f irradiating all spots on the solid phase with light in a first wavelength band to crosslink the nucleic acid linker and the mRNA and crosslink the nucleic acid linker and the reverse transcription primer;

(E6) synthesizing cDNA which is obtained such that a complementary strand is elongated from the 3'-terminal of the reverse transcription primer by subjecting the mRNA-nucleic acid linker-protein- or peptide-reverse transcription primer complex to a reverse transcription reaction to produce an mRNA/cDNA-nucleic acid linker-protein or peptide complex;

(F6) subjecting the solid phase, on which the mRNA/cDNA-nucleic acid linker-protein or peptide complex is immobilized, to functional screening to specify a spot on the solid phase;

(G6) irradiating the spot, which is specified through the functional screening, with light in a second wavelength band to dissociate the cDNA from the cDNA-nucleic acid linker-protein or peptide complex in the specified spot; and (H6) recovering the dissociated cDNA to analyze a base sequence thereof.

Hereinafter, the method of identifying a functional protein of the present embodiment will be described in detail, but the description of operations the same as those described above will not be repeated.

The functional screening in the (F6) is not particularly limited as long as the functional screening is performed for specifying a spot which has a desired protein from a large number of spots on the solid phase.

For example, in a case where a protein to be screened is an enzyme, examples of the functional screening include an enzyme activity measurement system. Specific examples of the technique include a technique of measuring an activity of a protein on a solid phase by preparing micro intaglio which has a fine recessed portion corresponding to a spot on the solid phase and filling the fine recessed portion of the micro intaglio with a solution (enzyme activity measurement system) which is required for measuring the activity of the protein, in advance, and causing an enzyme reaction by making the solid phase and the micro intaglio overlap each other.

In addition, as the method of measuring enzyme activity, a method which is well known in the related art is used and examples thereof include fluorescence resonance energy transfer (FRET method), an evanescent field molecule imaging method, a fluorescence imaging analysis method, a solid phase enzyme immunoassay method (enzyme-linked immunosorbent assay (ELISA)), a fluorescence depolarization method, fluorescent correlation spectroscopy, and a surface Plasmon resonance method.

The method of identifying a functional protein of the present embodiment may comprise (I6) of dissociating the mRNA from the mRNA/cDNA-nucleic acid linker-protein or peptide complex between the (F6) and the (G6). This is because it is necessary to first dissociate mRNA which forms a complementary strand, in order to recover the cDNA. The dissociation method is not particularly limited, and examples thereof include a dissociation method using heat or a denaturing agent or a dissociation method through decomposition of mRNA using RNase or an alkaline solution.

In the (G6), the crosslinking formed in the (D6) is released through irradiation with light in a second wavelength band which is different from a first wavelength band. According to the method of identifying a functional protein of the present embodiment, it is possible to selectively recover the cDNA which is dissociated through irradiation with light in a second wavelength band.

In the (H6), the dissociated cDNA is recovered. The recovery method is not particularly limited and examples thereof include a method, such as elution through heat treatment or using a urea-containing buffer, which is well known in the related art. Next, it is possible to identify DNA which encodes a protein or a peptide having a desired function, by analyzing the base sequence of the recovered cDNA.

Second Embodiment

Figure 10:
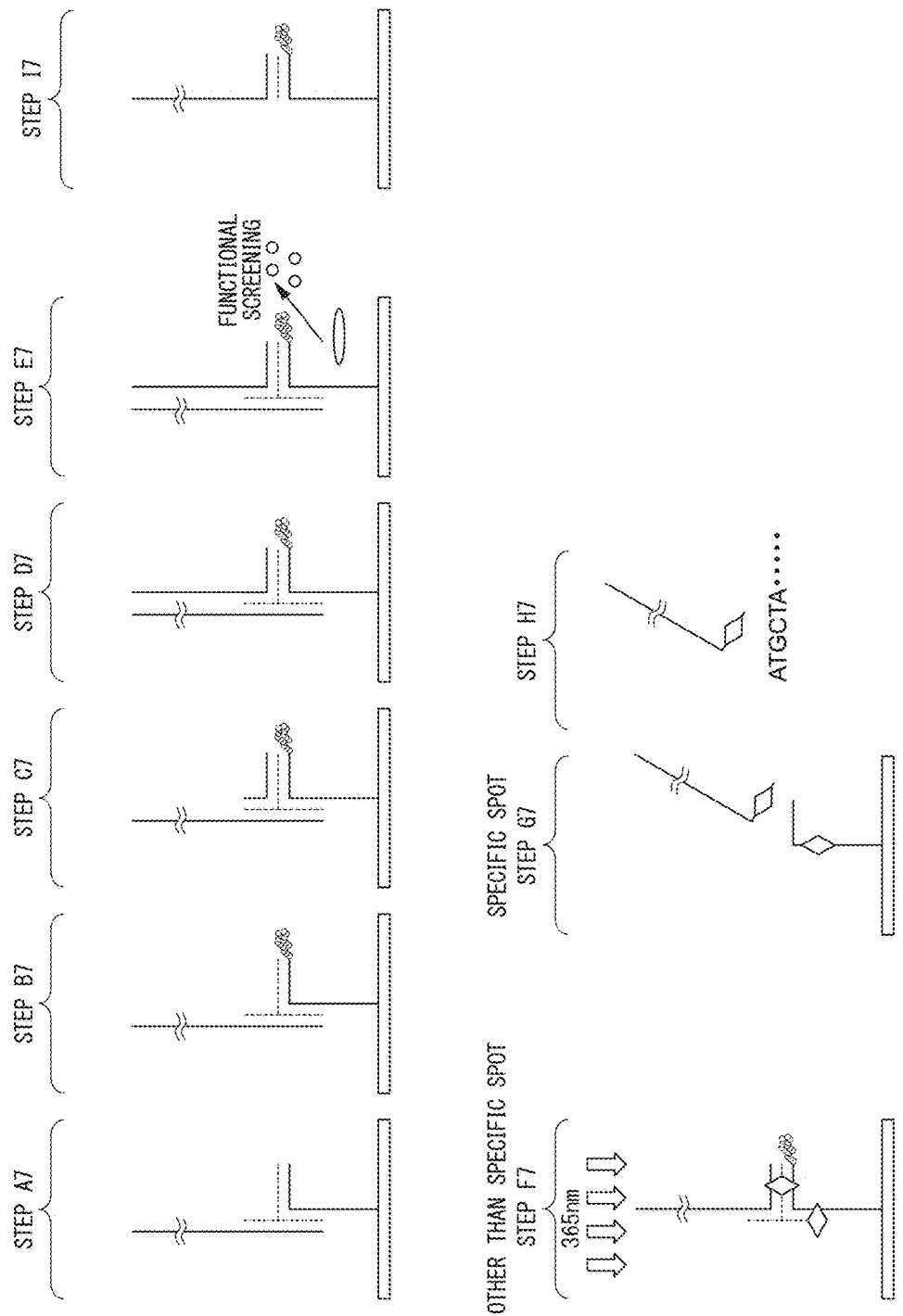
FIG. 10 is a view showing a mode of method of identifying a functional protein or a functional peptide of the present invention.

As shown in FIG. 10, a method of identifying a functional protein of the present embodiment comprises:

(A7) bringing mRNA into contact with a nucleic acid linker-immobilized solid phase of the present embodiment and hybridizing the mRNA with the nucleic acid linker to form an mRNA-nucleic acid linker complex on the solid phase;

(B7) synthesizing a protein or a peptide from the mRNA using a cell-free protein translation system and bonding the C-terminal of the protein or the peptide to a connection portion for the protein or the peptide to form an mRNA-nucleic acid linker-protein or peptide complex;

(C7) bringing a reverse transcription primer, which is formed of a 5'-terminal region portion having a sequence hybridizable with at least a part of a sequence of an arm portion of the nucleic acid linker, and contains 3-cyanovinylcarbazole nucleoside, and a 3'-terminal region portion having a sequence hybridizable with at least a part of a sequence of the mRNA, into contact with the solid phase to form an mRNA-nucleic acid linker-protein- or peptide-reverse transcription primer complex;

(D7) synthesizing cDNA which is obtained such that a complementary strand is elongated from the 3'-terminal of the reverse transcription primer by subjecting the mRNA-nucleic acid linker-protein- or peptide-reverse transcription primer complex to a reverse transcription reaction to produce an mRNA/cDNA-nucleic acid linker-protein or peptide complex;

(E7) subjecting the solid phase, on which the mRNA/cDNA-nucleic acid linker-protein or peptide complex is immobilized, to functional screening to specify a spot on the solid phase;

(F7) irradiating a spot other than the spot, which is specified through the functional screening, with light in a first wavelength band to crosslink the nucleic acid linker and the cDNA;

(G7) dissociating the cDNA from the cDNA-nucleic acid linker-protein or peptide complex in the specified spot; and (H7) recovering the dissociated cDNA to analyze a base sequence thereof.

Hereinafter, the method of identifying a functional protein of the present embodiment will be described in detail, but the description of steps the same as those described above will not be repeated.

The method of identifying a functional protein of the present embodiment may comprise (I7) dissociating the mRNA from the mRNA/cDNA-nucleic acid linker-protein or peptide complex between the (E7) and the (F7). This is because it is necessary to first dissociate mRNA which forms a complementary strand, in order to recover the cDNA. The dissociation method is not particularly limited, and examples thereof include a dissociation method using heat or a denaturing agent or a dissociation method through decomposition of mRNA using RNase or an alkaline solution.

In the present embodiment, in the (F7), the spot other than the specific spot on the solid phase is selectively irradiated with light in a first wavelength band, and the nucleic acid linker and the cDNA are crosslinked. Next, in the (G7), the cDNA is dissociated from a nucleic acid linker in a spot which is not irradiated with light in a first wavelength band. The dissociation method is the same as that in the first embodiment. According to the method of identifying a functional protein of the present embodiment, it is possible to selectively recover the cDNA which is not irradiated with light in a first wavelength band and to identify DNA which encodes a protein or a peptide having a desired function, by releasing the base sequence of the recovered cDNA.

Hereinafter, the present invention will be described through an example, but is not limited to the following example.

Example

Synthesis of Photocrosslinked Nucleic Acid Linker

The material shown below is manufactured by Tsukuba Oligo Service Co., Ltd., and is synthesized through a phosphoroamidite method using an automatic nucleic acid synthesis device.

(1) Photocrosslinked Nucleic Acid Linker 1 [Sequence: 5'-(HO—$C_6H_{12}$—SS—$C_6H_{12}$)—X1-(CNVK)-X2-(spc18)-(spc18)-(spc18)-CC-(Puromycin)-3']

X1 represents the following sequence.

(SEQ ID No: 1: 54 mer)
TTTTTTTTTTTTTTTTTTTTTTTTTTTTTTTTTTTTTTTTTTTTTTTTTT

TGCA

X2 represents the following sequence.

CCGTGTAGTAGTCGC     (SEQ ID No: 2: 15 mer)

(2) Photocrosslinked Nucleic Acid Linker 2 [Sequence: 5'-(HO—$C_6H_{12}$—SS—$C_6H_{12}$)—X3-(CNVK)-X4-(spc18)-(spc18)-(spc18)-CC-(Puromycin)-3']

X3 represents the following sequence.

(SEQ ID No: 3: 67 mer)
TTTTTTTTTTTTTTTTTTTTTTTTTTTTTTTTTTTTTTTTTTTTTTTTTTTT

TCAGATCACTCGGTCGA

X4 represents the following sequence.

GTAGACCGGTCTCG     (SEQ ID No: 4: 14 mer)

(3) Reverse Transcription Primer 1 [Sequence: 5'-X5-[CNVK]-X6-3']

X5 represents the following sequence.

CGAGA     (SEQ ID No: 5: 5 mer)

X6 represents the following sequence.

CGGTGACGATGCCT     (SEQ ID No: 6: 14 mer)

Here, the (HO—C$_6$H$_{12}$—SS—C$_6$H$_{12}$) represents a state of being synthesized using (1-O-dimethoxytrityl-hexyl-disulfide,1'-[(2-cyanoethyl)-(N,N-diisopropyl)]-phosphoramidite) (manufactured by Glen Research Corporation, trade name: Thiol-Modifier C6 S-S).

The (CNVK) represents a substance being synthesized using (3-cyanovinylcarbazole nucleoside, 1'-[(2-cyanoethyl)-(N,N-diisopropyl)]-phosphoramidite).

The (spc18) represents a substance being synthesized using 18-O-Dimethoxytritylhexaethyleneglycol,1-[(2-cyanoethyl)-(N,N-diisopropyl)]-phosphor amidite (manufactured by Glen Research Corporation, trade name: Spacer Phosphoramidite 18).

The (Puromycin) represents a substance being synthesized using 5'-dimethoxytrityl-N-trifluoroacetyl-puromycin, 2'-succinoyl-long chain alkylamino-CPG (manufactured by Glen Research Corporation, trade name: Puromycin-CPG).

[Synthesis of mRNA]

A T7 promoter sequence, a translation enhancer sequence, a sequence (hereinafter, referred to as PDO) which encoded Oct-1 POU-specific domain, a double strand DNA sequence (DNA 1, SEQ ID No: 7: 389 bp) which had a spacer region and a complementary strand region for a photocrosslinked linker 1, or a double strand DNA sequence (DNA 2, SEQ ID No: 8: 401 bp) which had a complementary strand region for photocrosslinked linkers 2 and 3 was amplified through PCR from the 5' upstream.

5-30 pmol/μl of mRNA was synthesized from the DNA which was obtained through PCR in accordance with the attached protocol using T7 RiboMAX Express Large Scale RNA Production System (manufactured by Promega Corporation) (RNA 1, SEQ ID No: 9: 359 mer, RNA 2, SEQ ID No: 10: 371 mer). Cy3-modified or Cy5-modified mRNA was produced by adding Cy3-UTP or Cy5-UTP (all are manufactured by GE Healthcare) to the mRNA synthesis reaction system.

[Photocrosslinking of Photocrosslinked Linker and mRNA in Liquid Phase]

(1) Reduction of Photocrosslinked Linker 1

2 μl of a 100 μM photocrosslinked linker 1 was mixed with 38 μl of 1 M of a phosphoric acid buffer (pH 9.0), 10 μl of 1 MDTT was added, the mixture was reacted for one hour at room temperature, and a disulfide group on the 5' side of the photocrosslinked linker 1 was reduced into a thiol group. Then, excessive DTT was removed using Micro Bio-Spin 6 Columns (manufactured by Bio-Rad Laboratories, Inc.) which was equilibrated using a 20 mM phosphoric acid buffer (pH 7.2).

(2) Tetramethylrhodamine Modification of the Reduced Photocrosslinked Linker 1

60 μl of the reduced photocrosslinked linker 1 was mixed with 5 μl of 1 mM tetramethylrhodamine-5-maleimide (manufactured by Wako Pure Chemical Industries, Ltd.) which was dissolved in DMSO and the mixture was reacted for 60 minutes at room temperature while being stirred well. Then, ethanol precipitation was performed to precipitate the reaction product, and unreacted tetramethylrhodamine-5-maleimide was removed. The precipitate was dissolved in 20 μl of nuclease-free water after being washed with 200 μl of 70% ethanol.

(3) Photocrosslinking of mRNA and the Tetrarhodamine-Modified Photocrosslinked Linker 1

5 pmol of the tetrarhodamine-modified photocrosslinked linker 1 and 15 pmol of mRNA were mixed in 10 μl of 50 mM Tris-HCL (pH 7.5)/2 M NaCl and the mixture was denatured by heat for 30 seconds at 90° C. Then, the mixture was hybridized by being slowly cooled to 10° C. over 13 minutes. Thereafter, irradiation with ultraviolet ray of 365 nm (210 mW/cm$^2$) was performed for 30 seconds.

The sample irradiated with an ultraviolet ray and the sample before ultraviolet ray irradiation were separated through 8 M urea/5% polyacrylamide gel electrophoresis and the fluorescence of tetramethylrhodamine was observed (excitation wavelength: 533 nm, fluorescence filter: 580 BP 30) using a fluorescence imager (Typoon 9410, manufactured by GE Healthcare). Then, the samples were stained with SYBR Gold (manufactured by Invitrogen™) and observed by the fluorescence imager (excitation wavelength: 488 nm, fluorescence filter: 520 BP 40).

Figure 11:
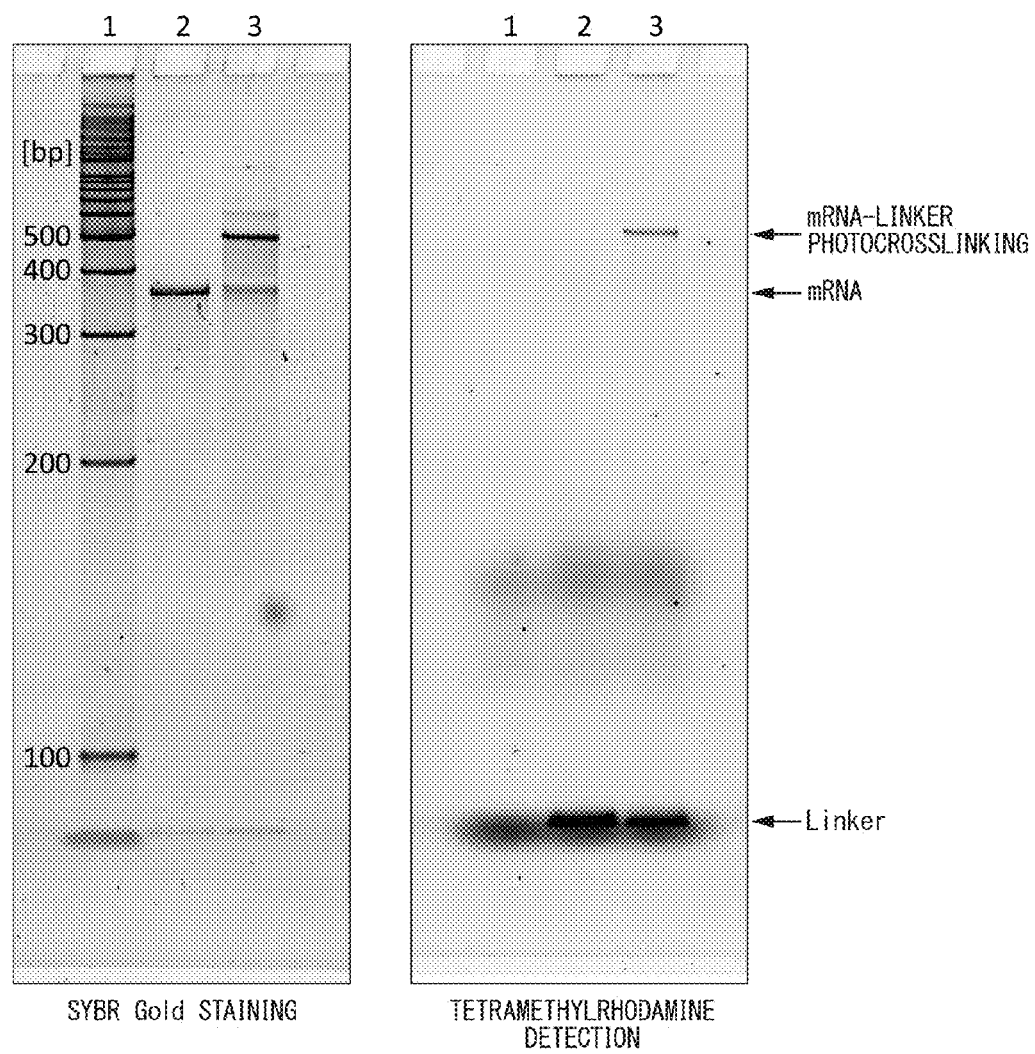
FIG. 11 is a result of electrophoresis in the example.

The results are shown in FIG. 11. Lane 1 is a 100 bp DNA ladder (manufactured by Promega Corporation), lane 2 is the sample before ultraviolet ray irradiation, and lane 3 is the sample irradiated with an ultraviolet ray. The left drawing is a view in which the fluorescence of the SYBR Gold staining is observed and the right drawing is a view in which the fluorescence of tetramethylrhodamine is observed. It was confirmed from lanes 2 and 3 that the tetramethylrhodamine-modified photocrosslinked linker 1 is photocrosslinked with mRNA through ultraviolet ray irradiation so that the molecular weight is increased.

[Connection Between mRNA and Protein Using Rabbit Reticulocyte Extract-Derived Cell-Free Translation System]

A translation reaction was performed using a photocrosslinked substance (photocrosslinked substance 1), which were synthesized as described above, of the photocrosslinked nucleic acid linker 1 and mRNA and using a rabbit reticulocyte extract-derived cell-free translation system. Nuclease-free water was added to 1 pmol of the photocrosslinked substance 1, 0.6 μl of 20× Translation Mix (manufactured by Life Technologies Corporation), 8.5 μl of Rabbit Reticulocyte Lysate (manufactured by Life Technologies Corporation) which is a cell lysis solution of rabbit net-like erythrocytes, and 0.25 μl of Fluorotect (manufactured by Promega Corporation), and the mixture was mixed to make 12.5 μl of a mixed liquid.

After the mixed liquid was reacted for 20 minutes at 30° C., 5 μl of 3 M potassium chloride solution and 1.5 μl of 1 M magnesium chloride solution were added thereto and the mixture was mixed. The mixed liquid was reacted for 30 minutes at 37° C., and a polypeptide strand of a PDO gene was synthesized to form a photocrosslinked substance 1-protein complex. The reaction product was separated through 8 M urea-containing SDS-6% polyacrylamide gel electrophoresis, and a fluorescence signal of tetramethylrhodamine of the photocrosslinked substance 1 and a fluorescence signal of Fluorotect which was incorporated into a protein were detected using a fluorescence imager.

[Connection Between mRNA and Protein Using Wheat Germ-Derived Cell-Free Translation System]

A translation reaction was performed using the photocrosslinked substance 1 which was synthesized as described above and using a wheat germ-derived cell-free translation system. Nuclease-free water was added to 1 pmol of the photocrosslinked substance 1, 0.5 μl of Amino Acid Mixture (manufactured by Promega Corporation), 6.25 μl of Wheat Germ Extract (manufactured by Promega Corporation) which is a wheat germ extract, 0.3 μl of Fluorotect (manufactured by Promega Corporation), 1.0 μl of potassium acetate, 0.2 μl of SUPERase•In (20 U/μl, manufactured by Life Technologies Corporation), and 0.2 μl of RNasin Plus RNase Inhibitor (manufactured by Promega Corporation), and the mixture was mixed to make 13 μl of a mixed liquid.

The mixed liquid was reacted for 20 minutes at 25° C., and a polypeptide strand of a PDO gene was synthesized to form a photocrosslinked substance 1-protein complex. The reaction product was separated through 8 M urea-containing SDS-6% polyacrylamide gel electrophoresis, and a fluorescence signal of tetramethylrhodamine of the photocrosslinked substance 1 and a fluorescence signal of Fluorotect which was incorporated into a protein were detected using a fluorescence imager.

[Experimental Results of Connecting mRNA and Protein in Liquid Phase]

Figure 12:
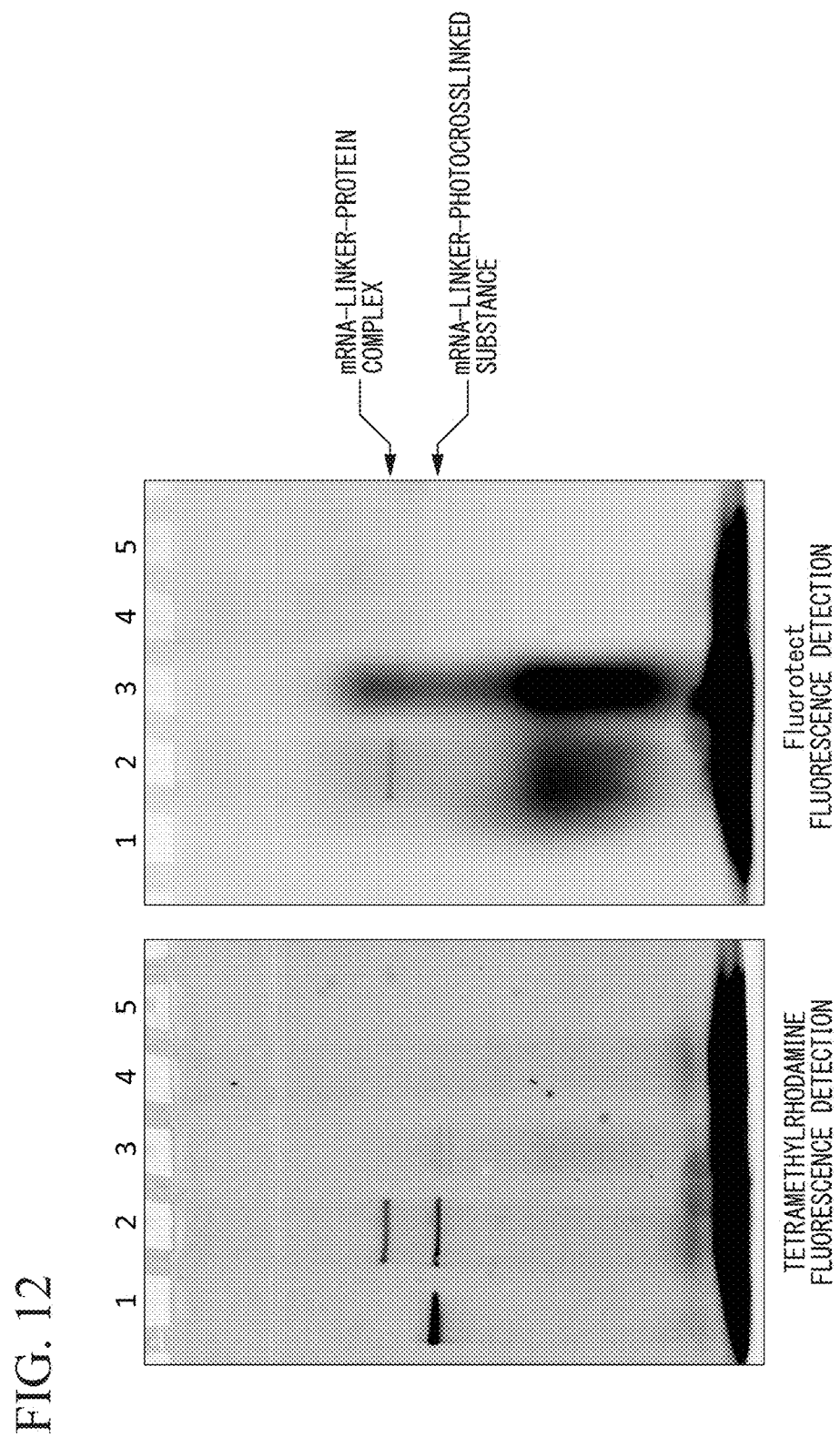
FIG. 12 is a result of electrophoresis in the example.

Experiment results of connecting mRNA and a protein using the above-described rabbit reticulocyte extract-derived cell-free translation system and wheat germ-derived cell-free translation system are shown in FIG. 12. Lane 1 is a photocrosslinked substance (photocrosslinked substance 1) of mRNA and a photocrosslinked linker 1, lane 2 is a translation product using the rabbit reticulocyte extract-derived cell-free translation system, lane 3 is a translation product using the wheat embryo-derived cell-free translation system, lane 4 is a reaction product of rabbit reticulocyte extract-derived cell-free translation system to which the photocrosslinked substance 1 and Fluorotect are not added, and lane 5 is a reaction product of wheat germ-derived cell-free translation system to which the photocrosslinked substance 1 and Fluorotect are not added. The left drawing is a view in which the fluorescence of tetramethylrhodamine of the photocrosslinked substance 1 is detected and the right drawing is a view in which the fluorescence of Fluorotect which is incorporated into the protein is detected (excitation wavelength: 488 nm, Fluorescence filter: 520 BP 40).

From the phoresis results, it was possible to confirm a band of the photocrosslinked substance 1-protein complex with the fluorescence signals of tetramethylrhodamine and Fluorotect on a higher molecular weight side than the photocrosslinked substance 1, in the reaction using the rabbit reticulocyte extract-derived cell-free translation system. In addition, in the reaction using the wheat germ-derived cell-free translation system, it was confirmed that the mRNA was decomposed in the reaction process. From the results, it was confirmed that it was preferable to use the rabbit reticulocyte extract-derived cell-free translation system in the reaction of forming an mRNA-protein complex using the photocrosslinked nucleic acid linker 1.

[Immobilization of Photocrosslinked Linker 1 on Gold Thin Film Substrate]

A gold thin film substrate was immersed in an acid solution ($H_2SO_4$:$H_2O_2$=1:1) and was washed for 15 minutes at 200° C. Then, the gold thin film substrate was rinsed with ultrapure water for 10 minutes and was dried by nitrogen gas.

Thereafter, a 1 µM reduced photocrosslinked linker 1 which was dissolved in 1×PBS was dripped on the gold thin film substrate to be reacted in a sealed reaction solution for 24 hours at room temperature.

Thereafter, the gold thin film substrate was immersed in 1 mM of 6-mercapto-1-hexanol solution which was dissolved in 10 ml of 1×PBS and was reacted for 1 hour at room temperature. Then, the gold thin film substrate was subjected to ultrasonic cleaning in 1×PBS/0.2% (v/v) Tween 20 solution for 30 minutes and was dried using a spin drier under conditions of 1000 rpm for 3 seconds and 3000 rpm for 20 seconds.

[Photocrosslinking mRNA on Gold Thin Film Substrate]

1 µM Cy3-modified mRNA 1 which was dissolved in 50 µl of 3×SSC containing 0.02% SDS was dripped on the entire surface of a gold thin film substrate on which a photocrosslinked linker 1 was immobilized. Then, mRNA 1 was hybridized with the photocrosslinked linker 1 by causing a reaction in a sealed container for 2 hours at 30° C. Then, unreacted mRNA was washed away by washing the gold thin film substrate in a 3×SSC solution for 5 minutes, in a 0.1×SSC/0.1% SDS solution for 5 minutes, and in a 0.1×SSC solution for 5 minutes.

Thereafter, the gold thin film substrate was spot-irradiated with an ultraviolet ray (210 mW/cm$^2$) of 365 nm for 1 second, 5 seconds, 10 seconds, 20 seconds, 30 seconds, 45 seconds, 60 seconds, and 90 seconds.

Thereafter, the hybridization of the photocrosslinked linker 1 and the mRNA 1 was released through washing using a 8 M urea solution, mRNA which was not photocrosslinked was washed away, and the Cy3-modified mRNA which remained on the gold thin film substrate and was photocrosslinked was observed by a fluorescence imager (excitation wavelength: 532 nm, fluorescence filter: 580 BP 30).

Figure 13:
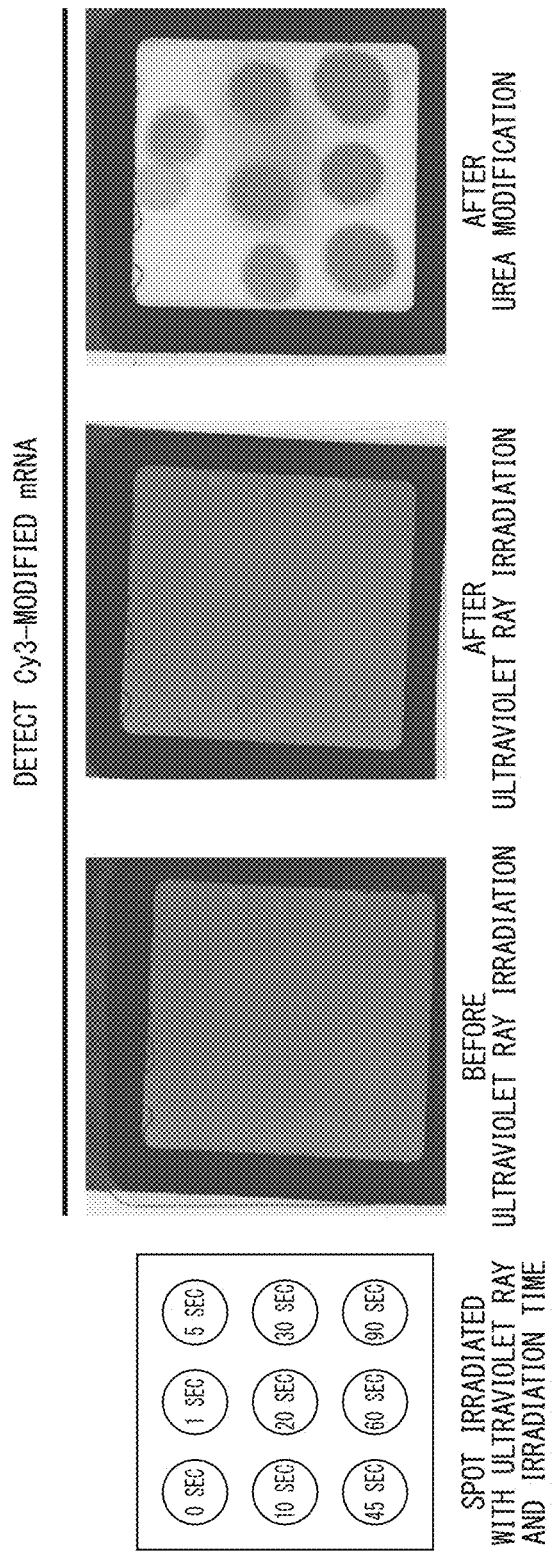
FIG. 13 is an analysis result using a fluorescence imager in the example.
Figure 14:
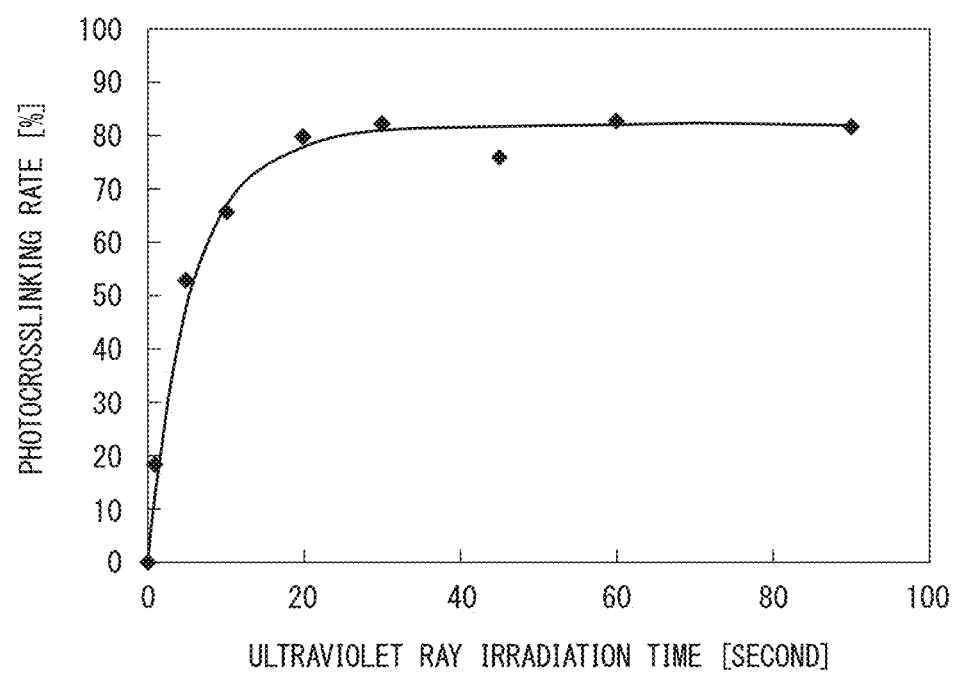
FIG. 14 is a result of quantitatively determining Cy3-modified mRNA in the example.

The results are shown in FIG. 13 which shows, from the left, a correspondence view between a spot irradiated with an ultraviolet ray and irradiation time, and Cy3 fluorescent images before ultraviolet ray irradiation was performed, after ultraviolet ray irradiation was performed, and after urea-washing. From the results, it was confirmed that Cy3-modified mRNA remained and photocrosslinking was performed only in spots which were irradiated with an ultraviolet ray. In addition, the amount of the remaining Cy3-modified mRNA was quantitatively determined, and as a result, it was confirmed that the photocrosslinking degree increased in accordance with the irradiation time (FIG. 14).

[Immobilization of Protein on Gold Thin Film Substrate]

1 µM Cy5-modified mRNA 1, a mixed liquid of 0.5 µM Cy5-modified mRNA 1 and 0.5 µM unmodified mRNA 1, a mixed liquid of 0.25 µM Cy5-modified mRNA 1 and 0.25 µM unmodified mRNA 1, and 1 µM unmodified mRNA 1, which were dissolved in 3×SSC, were spotted on a gold thin film substrate, onto which a photocrosslinked linker 1 was immobilized, by 5 µl each. Then, the mixture was reacted in a sealed container for 2 hours at 30° C., and was washed in a 3×SSC solution for 5 minutes, in a 0.1×SSC/0.1% SDS solution for 5 minutes, and in a 0.1×SSC solution for 5 minutes. Thereafter, the entire gold thin film substrate was irradiated with an ultraviolet ray (210 mW/cm$^2$) of 365 nm for 30 seconds, and the gold thin film substrate was observed by a fluorescence imager.

Next, the gold thin film substrate was washed with a washing liquid (80 mM potassium acetate and 0.5 mM magnesium acetate). Then, 50 µl of a rabbit reticulocyte extract-derived cell-free translation system (manufactured by Life Technologies Corporation) to which Fluorotect (manufactured by Promega Corporation) was added was dripped to cause a reaction in a sealed container for 20 minutes at 30° C. Thereafter, 25 µl of a high salt concentration solution (3 M potassium chloride and 1 M magnesium chloride) was added thereto to cause a reaction in a sealed container for 90 minutes at 37° C. Then, the gold thin film substrate was washed with a washing liquid (790 mM potassium chloride, 79 mM magnesium chloride, 52 mM potassium acetate, and 0.32 M magnesium acetate) and was observed by a fluorescence imager (Typhoon 9410, manufactured by GE Healthcare). The fluorescence (excitation wavelength: 633 nm, fluorescence filter: 670 BP 30) of the Cy5-modified mRNA 1 and the fluorescence of the Fluorotect which was incorporated into a protein were confirmed.

Then, the gold thin film substrate was washed with a magnesium-free washing liquid (790 mM potassium chloride and 52 mM potassium acetate) and was observed by a fluorescence imager (Typhoon 9410, manufactured by GE Healthcare) similarly to the above.

Figure 15:
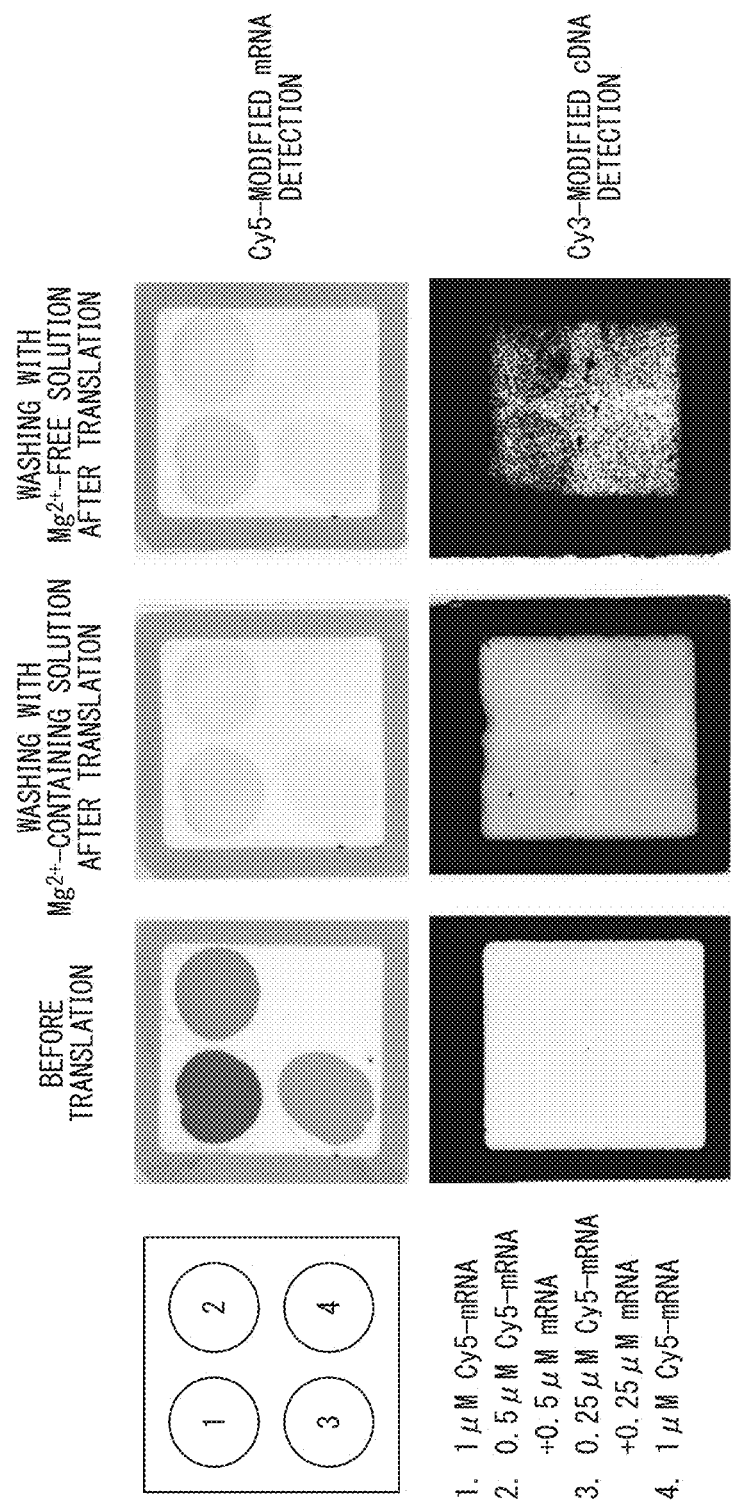
FIG. 15 is an analysis result using a fluorescence imager in the example.

The results are shown in FIG. 15. From the results, it can be seen that the protein into which the Fluorotect was incorporated exists on the same spot as that of the mRNA 1 after translation. In addition, when the gold thin film substrate was washed with the magnesium-free washing liquid, the fluorescence intensity of the Fluorotect greatly decreases. This was considered that polysome was washed away by the magnesium-free washing liquid, and as a result, the protein which had been bound to the mRNA through polysome existing on the mRNA and into which the Fluorotect was incorporated was also washed away at the same time. Moreover, it is considered that the Fluorotect-modified protein remaining on the gold thin film substrate even after being washed with the magnesium-free washing liquid is a protein which is bound to the mRNA 1 through the photocrosslinked linker 1. It was confirmed that it was possible to immobilize the protein on the substrate using the photocrosslinked linker 1.

[Reverse Transcription on Substrate]

A mixed liquid of 1 μM Cy5-modified mRNA 2 and 1 μM reverse transcription primer 1 which was dissolved in 3×SSC was dripped on four sites on a gold thin film substrate, onto which a photocrosslinked linker 2 was immobilized, by 5 μl to cause a reaction in a sealed container for 2 hours at 30° C. Then, the gold thin film substrate was washed in a 3×SSC solution for 5 minutes, in a 0.1×SSC/0.1% SDS solution for 5 minutes, and in a 0.1×SSC solution for 5 minutes.

Next, after the entire surface of the gold thin film substrate was irradiated with an ultraviolet ray (210 mW/cm$^2$) of 365 nm for 30 seconds, 50 μl of a SuperScript III reverse transcription reaction liquid (manufactured by Invitrogen™) to which Cy3-dCTP (manufactured by GE Healthcare) was added was dripped on the entire surface of the gold thin film substrate to cause a reaction in a sealed container for 1 hour at 42° C. Then, the gold thin film substrate was washed in a 3×SSC solution for 5 minutes, in a 0.1×SSC/0.1% SDS solution for 5 minutes, and in a 0.1×SSC solution for 5 minutes, and was observed by a fluorescence imager (Typhoon 9410, manufactured by GE Healthcare). The fluorescence of the Cy5-modified mRNA 2 and the fluorescence of Cy3 which was incorporated into cDNA during the reverse transcription reaction were confirmed.

Figure 16:
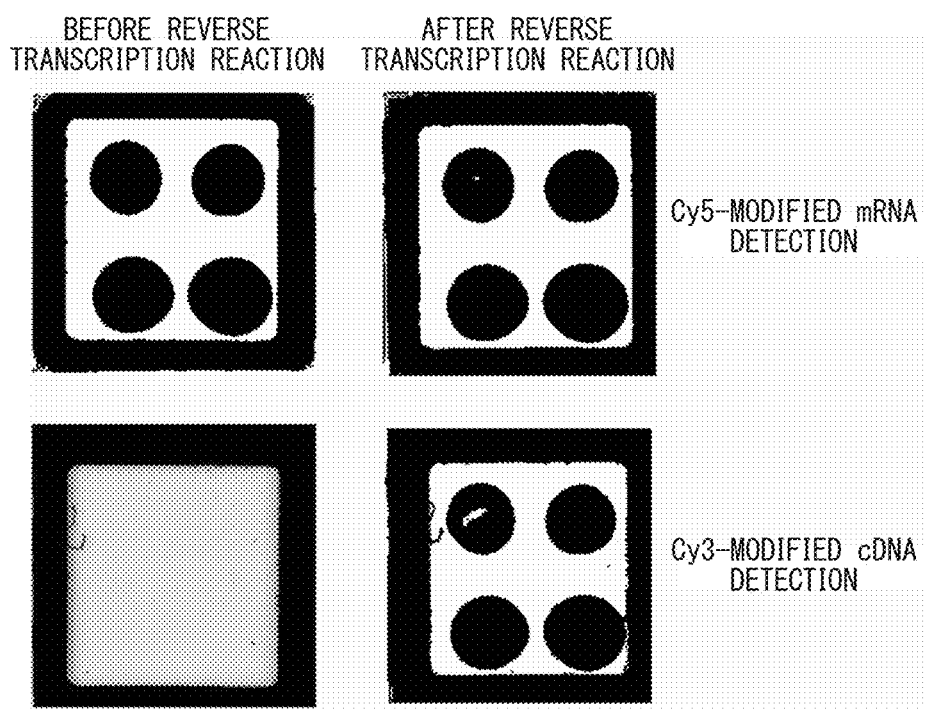
FIG. 16 is an analysis result using a fluorescence imager in the example.

The results are shown in FIG. 16. From the result, it can be confirmed that the Cy3-modified cDNA is synthesized on the substrate after the reverse transcription reaction.

[cDNA Recovery 1 from Top of Substrate]

100 units of ribonuclease 14 (manufactured by Takara Bio Inc.), which were dissolved in 1×PBS containing 50 μl of 4 mM magnesium chloride, were dripped on a gold thin film substrate, on which the reverse transcription reaction was performed, to cause a reaction in a sealed container for 15 minutes at 30° C. Then, decomposition of the Cy5-modified mRNA due to the ribonuclease H was confirmed by a fluorescence imager.

Figure 17:
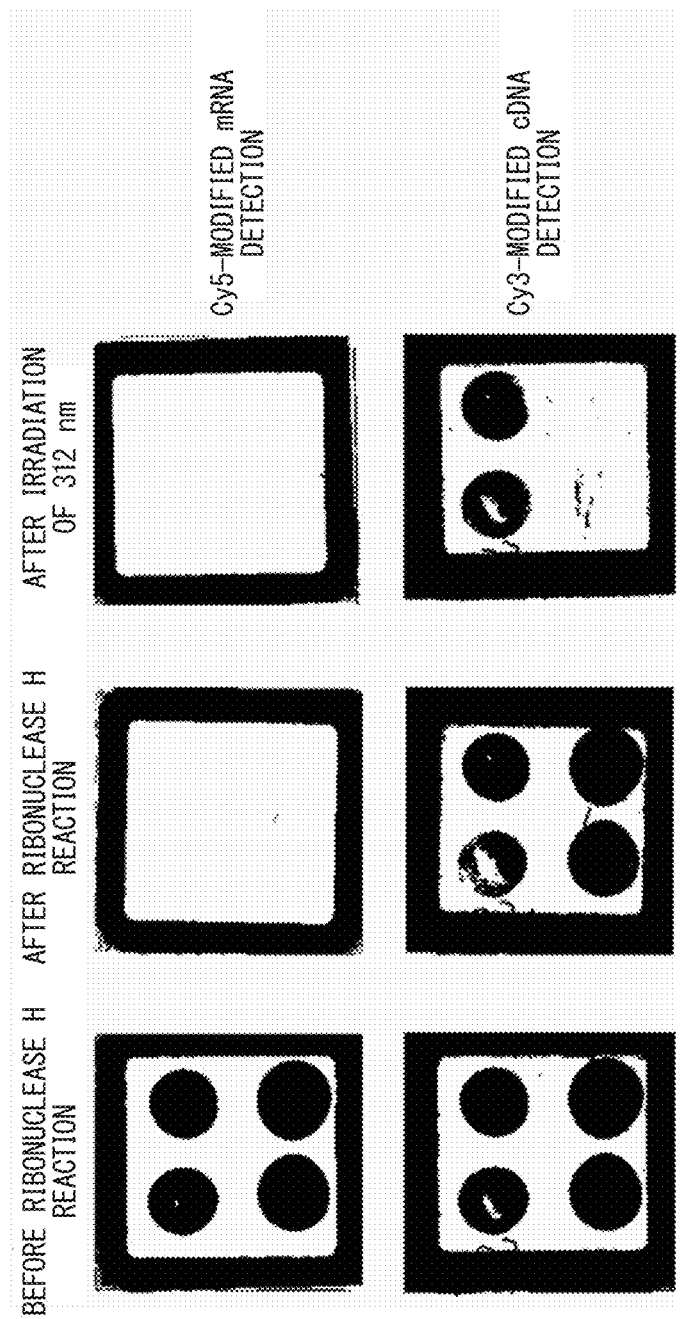
FIG. 17 is an analysis result using a fluorescence imager in the example.

The results are shown in FIG. 17. From the results, it can be confirmed that the Cy5-modified mRNA is decomposed and disappeared while the Cy3-modified cDNA remained.

Next, 50 μl of 8 M urea solution was dripped on the entire surface of the substrate and two spots out of Cy3-modified cDNA-immobilized spots were irradiated with an ultraviolet ray (10 mW/cm$^2$) of 312 nm for 180 seconds, and the whole solution on the substrate was then recovered.

The gold thin film substrate after recovering the solution was observed by a fluorescence imager and it was confirmed that the Cy3-modified cDNA was separated from the spots irradiated with the ultraviolet ray of 312 nm.

Figure 18:
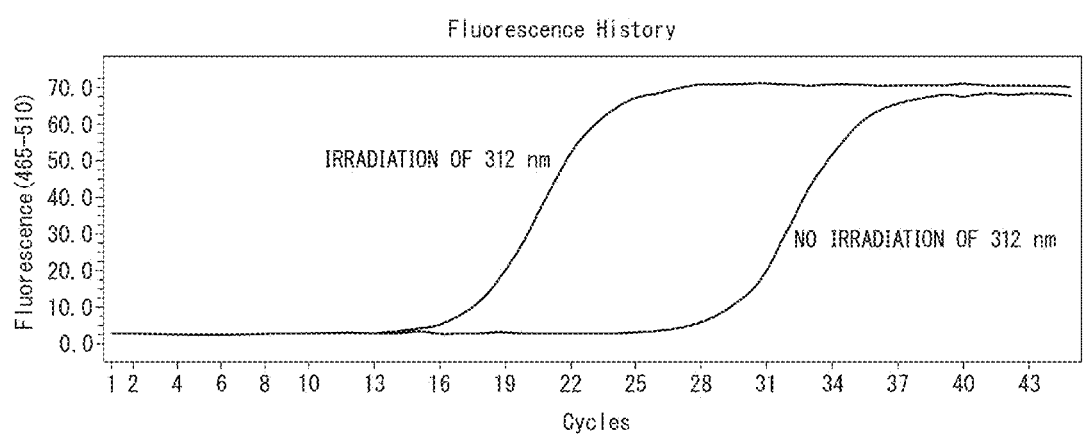
FIG. 18 is a result of quantitatively determining Cy3-modified DNA which is recovered in the example.

The recovered solution which was considered such that the Cy3-modified cDNA, which was separated through photo cleavage was dissolved, was concentrated through ethanol precipitation. Then, the amount of cDNA contained in the recovered solution was analyzed through real time PCR. As a result, the amount of DNA recovered was about 16000 molecules. The samples which were recovered without irradiation with an ultraviolet ray of 312 nm were quantitatively determined in the same manner. As a result, the amount of DNA was less than a quantitative determination range in a real time PCR experiment system using SYBR Green I while amplification of DNA was found (refer to FIG. 18). From the above, it was able to confirm the recovery of DNA from the top of the substrate depending on the irradiation of an ultraviolet ray of 312 nm. LightCycler 480 (manufactured by Roche Diagnostics K.K.) was used as a real time PCR device, LightCycler 480 SYBR Green I Master (manufactured by Roche Diagnostics K.K.) was used as a real time PCR reagent, and (5'-GACCTTGAGGAGCT-TGAGCAG-3' (SEQ ID NO: 11)) and (5'-ATAGCGAGC-CCAACATCACC-3' (SEQ ID NO: 12)) were used as primers.

Figure 19:
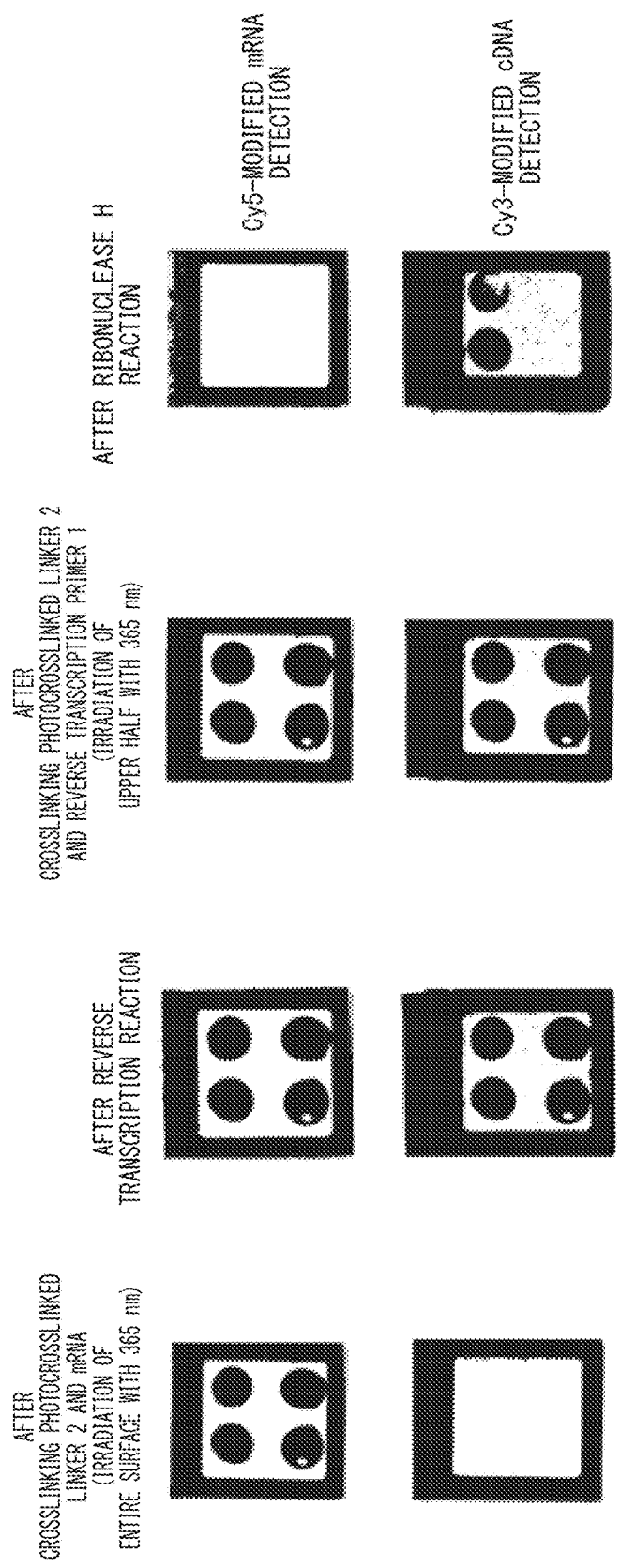
FIG. 19 is an analysis result using a fluorescence imager in the example.

A mixed liquid of 0.5 μM Cy5-modified mRNA 1 and 0.5 μM unmodified mRNA 1 which was dissolved in 3×SSC was spotted on four sites on a gold thin film substrate, onto which a photocrosslinked linker 2 was immobilized, by 5 μl. Then, the mixed liquid was reacted in a sealed container for 2 hours at 30° C., and was washed in a 3×SSC solution for 5 minutes, in a 0.1×SSC/0.1% SDS solution for 5 minutes, and in a 0.1×SSC solution for 5 minutes. Thereafter, the entire gold thin film substrate was irradiated with an ultraviolet ray (210 mW/cm$^2$) of 365 nm for 30 seconds in a 0.1×SSC solution, and the gold thin film substrate was observed by a fluorescence imager (refer to FIG. 19).

Next, 50 μl of a 2 μM of photocrosslinked linker 3 and 50 μl of a SuperScript III reverse transcription reaction liquid (manufactured by Invitrogen™) to which Cy3-dCTP (manufactured by GE Healthcare) was added was dripped on the entire surface of the gold thin film substrate to cause a reaction in a sealed container for 30 minutes at 30° C. and 1 hour at 42° C. Then, the gold thin film substrate was washed in a 3×SSC solution for 5 minutes, in a 0.1×SSC/0.1% SDS solution for 5 minutes, and in a 0.1×SSC solution for 5 minutes, and was observed by a fluorescence imager. The fluorescence of Cy5-modified mRNA and the fluorescence of Cy3 which was incorporated into cDNA during the reverse transcription reaction were confirmed (refer to FIG. 19). Thereafter, a part of the gold thin film substrate was irradiated with ultraviolet ray (210 mW/cm$^2$) of 365 nm for 30 seconds.

Next, 100 units of ribonuclease H (manufactured by Takara Bio Inc.), which were dissolved in 1×PBS containing 50 μl of 4 mM magnesium chloride, were dripped on a gold thin film substrate, on which the reverse transcription reaction was performed, to cause a reaction in a sealed container for 15 minutes at 30° C. and 5 minutes at 40° C., and the whole solution on the substrate was then recovered. Decomposition of the mRNA and separation of cDNA due to the ribonuclease H were confirmed by a fluorescence imager (refer to FIG. 19).

The gold thin film substrate after recovering the solution was observed by a fluorescence imager and it was confirmed that the Cy3-modified cDNA was separated from the spots which were not irradiated with the ultraviolet ray of 365 nm twice.

From the above results, it is obvious that, according to the nucleic acid linker of the present embodiment, it is possible to efficiently synthesize the mRNA-nucleic acid linker-protein or peptide complex on a solid phase.

In addition, it is obvious that, according to the nucleic acid recovery method of the present embodiment, it is possible to efficiently recover a nucleic acid from a specific region on the solid phase.

INDUSTRIAL APPLICABILITY

It is possible to provide a nucleic acid linker which can efficiently synthesize an mRNA-nucleic acid linker-protein or peptide complex on a solid phase.

REFERENCE SIGNS LIST 2, 12 nucleic acid linker
2a connection portion
23, 63 mRNA
33, 73 protein or peptide

What is claim is:

1. A nucleic acid linker for producing a complex of mRNA, and a protein or a peptide which is encoded by the mRNA, comprising:
   a spacer portion at the 5'-terminal;
   a polynucleotide portion hybridizable with at least a part of a sequence of the mRNA; and
   an arm portion which has a connection portion for the protein or the peptide at the 3'-terminal,
   wherein the spacer portion, the polynucleotide portion, and the arm portion form a single strand, and the polynucleotide portion contains a photoreactive base derivative, wherein the photoreactive base derivative is a 3-cyanovinylcarbazole nucleoside.

2. The nucleic acid linker according to claim 1, wherein the spacer portion has a bonding site with a solid phase at the 5'-terminal.

3. The nucleic acid linker according to claim 1, wherein the spacer portion has oligonucleotides with 50 or more bases.

4. The nucleic acid linker according to claim 1, further comprising:
   a branched strand which has the 3'-terminal protruding from a space between the polynucleotide portion and the arm portion, and has a primer sequence which is hybridized with a part of a sequence of the mRNA and reversely transcribes the mRNA.

5. A nucleic acid linker-reverse transcription primer complex comprising:
   the nucleic acid linker according to claim 1, and
   a reverse transcription primer of the mRNA, comprising a 5'-terminal region portion having a sequence hybridizable with at least a part of a sequence of the arm portion of the nucleic acid linker.

6. The nucleic acid linker-reverse transcription primer complex according to claim 5, wherein the reverse transcription primer includes a photoreactive base derivative in the 5'-terminal region portion.

7. A mRNA-nucleic acid linker-reverse transcription primer complex comprising:
   the nucleic acid linker-reverse transcription primer complex according to claim 5 and the mRNA,
   wherein the reverse transcription primer comprises a 3'-terminal region portion having a sequence hybridizable with at least a part of a sequence of the mRNA.

* * * * *

SEQUENCE LISTING

```
<160> NUMBER OF SEQ ID NOS: 15

<210> SEQ ID NO 1
<211> LENGTH: 54
<212> TYPE: DNA
<213> ORGANISM: Artificial Sequence
<220> FEATURE:
<223> OTHER INFORMATION: Description of Artificial Sequence: Synthetic
      X1 sequence

<400> SEQUENCE: 1
tttttttttt tttttttttt tttttttttt tttttttttt tttttttttt tgca          54

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      X2 sequence

<400> SEQUENCE: 2
ccgtgtagta gtcgc                                                     15

<210> SEQ ID NO 3
<211> LENGTH: 67
<212> TYPE: DNA
<213> ORGANISM: Artificial Sequence
<220> FEATURE:
<223> OTHER INFORMATION: Description of Artificial Sequence: Synthetic
      X3 sequence

<400> SEQUENCE: 3
tttttttttt tttttttttt tttttttttt tttttttttt tttttttttt tcagatcact    60
cggtcga                                                              67

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      X4 sequence

<400> SEQUENCE: 4
gtagaccggt ctcg                                                      14

<210> SEQ ID NO 5
<211> LENGTH: 5
<212> TYPE: DNA
<213> ORGANISM: Artificial Sequence
<220> FEATURE:
<223> OTHER INFORMATION: Description of Artificial Sequence: Synthetic
      X5 sequence

<400> SEQUENCE: 5 cgaga                                                                 5
```

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      X6 sequence

<400> SEQUENCE: 6
cggtgacgat gcct                                                          14

<210> SEQ ID NO 7
<211> LENGTH: 389
<212> TYPE: DNA
<213> ORGANISM: Artificial Sequence
<220> FEATURE:
<223> OTHER INFORMATION: Description of Artificial Sequence: Synthetic
      DNA1 sequence

<400> SEQUENCE: 7
gatcccgcga aattaatacg actcactata ggggaagtat ttttacaaca attaccaaca         60
acaacaacaa acaacaacaa cattacattt tacattctac aactacaagc caccatggac        120
cttgaggagc ttgagcagtt tgccaagacc ttcaaacaaa gacgaatcaa acttggattc        180
actcagggtg atgttgggct cgctatgggg aaactatatg gaaatgactt cagccaaact        240
accatctctc gatttgaagc cttgaacctc agctttaaga acatggctaa gttgaagcca        300
cttttagaga agtggctaaa tgatgcagag ggggaggca gccatcatca tcatcatcac         360
ggcggaagcg cgactactac acgggtgca                                          389

<210> SEQ ID NO 8
<211> LENGTH: 401
<212> TYPE: DNA
<213> ORGANISM: Artificial Sequence
<220> FEATURE:
<223> OTHER INFORMATION: Description of Artificial Sequence: Synthetic
      DNA2 sequence

<400> SEQUENCE: 8
gatcccgcga aattaatacg actcactata ggggaagtat ttttacaaca attaccaaca         60
acaacaacaa acaacaacaa cattacattt tacattctac aactacaagc caccatggac        120
cttgaggagc ttgagcagtt tgccaagacc ttcaaacaaa gacgaatcaa acttggattc        180
actcagggtg atgttgggct cgctatgggg aaactatatg gaaatgactt cagccaaact        240
accatctctc gatttgaagc cttgaacctc agctttaaga acatggctaa gttgaagcca        300
cttttagaga agtggctaaa tgatgcagag ggggaggca gccatcatca tcatcatcac         360
ggcggaagca ggcatcgtcc tacgtcgacc gagtgatctg a                            401

<210> SEQ ID NO 9
<211> LENGTH: 359
<212> TYPE: RNA
<213> ORGANISM: Artificial Sequence
<220> FEATURE:
<223> OTHER INFORMATION: Description of Artificial Sequence: Synthetic
      RNA1 sequence

<400> SEQUENCE: 9
ggggaaguau uuuuacaaca auuaccaaca acaacaacaa acaacaacaa cauuacauuu         60
uacauucuac aacuacaagc caccauggac cuugaggagc uugagcaguu ugccaagacc        120
uucaaacaaa gacgaaucaa acuuggauuc acucagggug auguugggcu cgcuauggg        180

```
aaacuauaug gaaaugacuu cagccaaacu accaucucuc gauuugaagc cuugaaccuc    240
agcuuuaaga acauggcuaa guugaagcca cuuuuagaga aguggcuaaa ugaugcagag    300
gggggaggca gccaucauca ucaucaucac ggcggaagcg cgacuacuac acgggugca    359

<210> SEQ ID NO 10
<211> LENGTH: 371
<212> TYPE: RNA
<213> ORGANISM: Artificial Sequence
<220> FEATURE:
<223> OTHER INFORMATION: Description of Artificial Sequence: Synthetic
      RNA2 sequence

<400> SEQUENCE: 10
ggggaaguau uuuuacaaca auuaccaaca acaacaacaa acaacaacaa cauuacauuu    60
uacauucuac aacuacaagc caccauggac cuugaggagc uugagcaguu ugccaagacc    120
uucaaacaaa gacgaaucaa acuuggauuc acucagggug auguuggcu cgcuauggg    180 aaacuauaug gaaaugacuu cagccaaacu accaucucuc gauuugaagc cuugaaccuc    240
agcuuuaaga acauggcuaa guugaagcca cuuuuagaga aguggcuaaa ugaugcagag    300
gggggaggca gccaucauca ucaucaucac ggcggaagca ggcaucgucc uacgucgacc    360
gagugaucug a    371

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaccttgagg agcttgagca g    21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atagcgagcc caacatcacc    20

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gcgacuacua cacggguugca    20

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 14
tcagatcact cggtcga                                                    17

<210> SEQ ID NO 15
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gcauggauga gcucuacaaa aggcaucguc cuacgucgac cgagugaucu ga             52
```